US006410303B1

(12) United States Patent
Takano et al.

(10) Patent No.: US 6,410,303 B1
(45) Date of Patent: *Jun. 25, 2002

(54) FROZEN DOUGH-RESISTANT, PRACTICAL BAKER'S YEAST

(75) Inventors: Hiroyuki Takano; Akihiro Hino; Chie Iyo, all of Ibaraki-ken; Yasuo Suzuki, Chiba-ken; Ryoichi Nakajima, Tokyo, all of (JP)

(73) Assignees: National Food Research Institute, Ministry of Agriculture, Forestry and Fisheries, Ibaraki-ken; Oriental Yeast Co., Ltd., Tokyo, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/969,415

(22) Filed: Oct. 21, 1997

(30) Foreign Application Priority Data

Oct. 23, 1996 (JP) .............................................. 8-297886

(51) Int. Cl.[7] .................................................. C12N 1/20
(52) U.S. Cl. .............................. 435/254.21; 435/254.11
(58) Field of Search ........................ 435/254.21, 172.3, 435/477, 254.11

(56) References Cited

U.S. PATENT DOCUMENTS

| | | | | |
|---|---|---|---|---|
| 4,547,375 A | * | 10/1985 | Nakatomi et al. | |
| 5,312,909 A | * | 5/1994 | Driessen et al. | |
| 5,578,461 A | * | 11/1996 | Sherwin et al. | 435/69.1 |
| 5,580,734 A | * | 12/1996 | Treco et al. | 435/6 |

FOREIGN PATENT DOCUMENTS

| | | |
|---|---|---|
| EP | 0451896 | 10/1991 |
| WO | 9317093 | 9/1993 |

OTHER PUBLICATIONS

Klaassen et al., Folia Microbiol. 39(6):524–526 (1994).*
Kopp, Meinrad et al., "Molecular analysis of the neutral trehalase gene from *Saccharomyces cerevisiae*.", The Journal of Biological Chemistry, vol. 268, No. 7, pp. 4766–4774 (1993).

Van Dijck, Patrick et al., "Differential importance of trehalose in stress resistance in fermenting and nonfermenting *Saccharomyces cerevisiae* Cells.", Applied and Environmental Microbiology, vol. 61, No. 1, pp. 109–115 (1995).

Rose, Mark et al., "Structure and function of the yeast URA3 gene: expression in *Escherichi coli*.", Gene, vol. 29, pp. 113–124 (1984).

Kim, John et al., "Disruption of the Yeast ATH1 Gene confers better survival after dehydration, freezing, and ethanol shock: potential commercial applications.", Applied and Environmental Microbiology, vol. 62, No. 5, pp. 1563–1569 (1996).

Meric, Laure et al., "Cryoresistance of baker's yeast *Saccharomyces cerevisiae* in frozen dough: contribution of cellular trehalose.", Cereal Chemistry, vol. 72, No. 6, pp. 609–615 (1995).

Hino, Akihiro, "Trehalose and stress resistance of yeast.", Journal of Brewing Society of Japan (1994). with translation of excerpt.

Van Laere, FEMS Microbiology Reviews 63:201–210 (1989).*

Smith et al. Histone H3 and H4 Gene Deletions in *Saccharomyces cerevsiae* Journal of Cell Biology vol. 106 Mar. 1988 557–566.*

* cited by examiner

Primary Examiner—Remy Yucel
(74) Attorney, Agent, or Firm—Browdy and Neimark

(57) ABSTRACT

The invention provides a diploid or higher polyploid, practical baker's yeast with good frozen dough resistance. This is produced through mating with one or more NTH1 gene-disrupted, haploid yeasts as produced through gene manipulation of disrupting the NTH1 gene in a haploid yeast of which the diploid is practical baker's yeast. The reduction in the trehalose content of the yeast is significantly prevented even when used in frozen dough, and the frozen dough containing the yeast is well resistant to long-term freezing and storage.

2 Claims, 18 Drawing Sheets

FIG. 1

| | | | | | | | | | | | | | | |
|---|---|---|---|---|---|---|---|---|---|---|---|---|---|---|
| ATG | AGT | CAA | GTT | AAT | ACA | AGC | CAA | GGA | CCG | GTA | GCC | CAA | GGC | CGT | 45 |
| Met | Ser | Gln | Val | Asn | Thr | Ser | Gln | Gly | Pro | Val | Ala | Gln | Gly | Arg | |
| | | | | 5 | | | | | 10 | | | | | 15 | |
| CAA | AGA | AGA | TTA | TCA | TCA | CTA | AGT | GAA | TTC | AAT | GAT | CCA | TTT | TCG | 90 |
| Gln | Arg | Arg | Leu | Ser | Ser | Leu | Ser | Glu | Phe | Asn | Asp | Pro | Phe | Ser | |
| | | | | 20 | | | | | 25 | | | | | 30 | |
| AAC | GCA | GAA | GTC | TAC | TAT | GGC | CCC | CCA | ACA | GAC | CCA | AGA | AAG | CAG | 135 |
| Asn | Ala | Glu | Val | Tyr | Tyr | Gly | Pro | Pro | Thr | Asp | Pro | Arg | Lys | Gln | |
| | | | | 35 | | | | | 40 | | | | | 45 | |
| AAG | CAG | GCA | AAG | CCC | GCT | AAG | ATC | AAC | CGT | ACG | AGG | ACT | ATG | AGT | 180 |
| Lys | Gln | Ala | Lys | Pro | Ala | Lys | Ile | Asn | Arg | Thr | Arg | Thr | Met | Ser | |
| | | | | 50 | | | | | 55 | | | | | 60 | |
| GTT | TTC | GAT | AAT | GTA | TCT | CCT | TTC | AAG | AAA | ACT | GGT | TTT | GGT | AAA | 225 |
| Val | Phe | Asp | Asn | Val | Ser | Pro | Phe | Lys | Lys | Thr | Gly | Phe | Gly | Lys | |
| | | | | 65 | | | | | 70 | | | | | 75 | |
| CTT | CAA | CAG | ACT | AGA | CGT | GGT | TCT | GAG | GAT | GAC | ACC | TAT | TCA | AGT | 270 |
| Leu | Gln | Gln | Thr | Arg | Arg | Gly | Ser | Glu | Asp | Asp | Thr | Tyr | Ser | Ser | |
| | | | | 80 | | | | | 85 | | | | | 90 | |
| AGT | CAA | GGT | AAT | CGT | CGT | TTC | TTT | ATC | GAA | GAT | GTC | GAT | AAA | ACA | 315 |
| Ser | Gln | Gly | Asn | Arg | Arg | Phe | Phe | Ile | Glu | Asp | Val | Asp | Lys | Thr | |
| | | | | 95 | | | | | 100 | | | | | 105 | |
| CTT | AAT | GAA | CTA | CTG | GCT | GCT | GAG | GAT | ACC | GAT | AAA | AAT | TAT | CAG | 360 |
| Leu | Asn | Glu | Leu | Leu | Ala | Ala | Glu | Asp | Thr | Asp | Lys | Asn | Tyr | Gln | |
| | | | | 110 | | | | | 115 | | | | | 120 | |
| ATC | ACC | ATC | GAG | GAT | ACC | GGT | CCA | AAA | GTT | TTG | AAA | GTC | GGT | ACC | 405 |
| Ile | Thr | Ile | Glu | Asp | Thr | Gly | Pro | Lys | Val | Leu | Lys | Val | Gly | Thr | |
| | | | | 125 | | | | | 130 | | | | | 135 | |
| GCA | AAC | TCC | TAT | GGC | TAT | AAG | CAT | ATT | AAT | ATT | AGG | GGT | ACG | TAT | 450 |
| Ala | Asn | Ser | Tyr | Gly | Tyr | Lys | His | Ile | Asn | Ile | Arg | Gly | Thr | Tyr | |
| | | | | 140 | | | | | 145 | | | | | 150 | |
| ATG | TTA | TCC | AAT | TTG | TTG | CAG | GAA | CTA | ACT | ATT | GCG | AAA | AGT | TTT | 495 |
| Met | Leu | Ser | Asn | Leu | Leu | Gln | Glu | Leu | Thr | Ile | Ala | Lys | Ser | Phe | |
| | | | | 155 | | | | | 160 | | | | | 165 | |
| GGT | AGA | CAC | CAA | ATT | TTC | TTA | GAT | GAA | GCT | CGT | ATA | AAC | GAA | AAT | 540 |
| Gly | Arg | His | Gln | Ile | Phe | Leu | Asp | Glu | Ala | Arg | Ile | Asn | Glu | Asn | |
| | | | | 170 | | | | | 175 | | | | | 180 | |
| CCC | GTC | AAC | AGA | TTA | TCA | AGA | TTG | ATA | AAC | ACA | CAG | TTC | TGG | AAC | 585 |
| Pro | Val | Asn | Arg | Leu | Ser | Arg | Leu | Ile | Asn | Thr | Gln | Phe | Trp | Asn | |
| | | | | 185 | | | | | 190 | | | | | 195 | |

FIG. 2

| | | | | | | | | | | | | | |
|---|---|---|---|---|---|---|---|---|---|---|---|---|---|
| TCT | TTG | ACC | AGG | AGA | GTT | GAT | CTG | AAC | AAC | GTA | GGC | GAA | ATT | GCA | 630
| Ser | Leu | Thr | Arg | Arg | Val | Asp | Leu | Asn | Asn | Val | Gly | Glu | Ile | Ala |
| | | | 200 | | | | | 205 | | | | | 210 | |
| AAA | GAT | ACC | AAG | ATT | GAT | ACG | CCG | GGG | GCA | AAA | AAT | CCA | AGA | ATC | 675
| Lys | Asp | Thr | Lys | Ile | Asp | Thr | Pro | Gly | Ala | Lys | Asn | Pro | Arg | Ile |
| | | | 215 | | | | | 220 | | | | | 225 | |
| TAT | GTT | CCT | TAT | GAT | TGT | CCA | GAA | CAA | TAC | GAA | TTT | TAT | GTT | CAA | 720
| Tyr | Val | Pro | Tyr | Asp | Cys | Pro | Glu | Gln | Tyr | Glu | Phe | Tyr | Val | Gln |
| | | | 230 | | | | | 235 | | | | | 240 | |
| GCT | TCT | CAA | ATG | CAT | CCA | TCT | TTG | AAA | TTA | GAA | GTT | GAA | TAT | TTA | 765
| Ala | Ser | Gln | Met | His | Pro | Ser | Leu | Lys | Leu | Glu | Val | Glu | Tyr | Leu |
| | | | 245 | | | | | 250 | | | | | 255 | |
| CCA | AAA | AAA | ATA | ACG | GCA | GAA | TAC | GTC | AAA | TCC | GTC | AAT | GAT | ACC | 810
| Pro | Lys | Lys | Ile | Thr | Ala | Glu | Tyr | Val | Lys | Ser | Val | Asn | Asp | Thr |
| | | | 260 | | | | | 265 | | | | | 270 | |
| CCC | GGT | TTA | CTA | GCA | TTG | GCT | ATG | GAA | GAG | CAC | TTC | AAT | CCT | TCT | 855
| Pro | Gly | Leu | Leu | Ala | Leu | Ala | Met | Glu | Glu | His | Phe | Asn | Pro | Ser |
| | | | 275 | | | | | 280 | | | | | 285 | |
| ACT | GGT | GAA | AAA | ACT | CTC | ATT | GGT | TAC | CCT | TAT | GCT | GTT | CCT | GGT | 900
| Thr | Gly | Glu | Lys | Thr | Leu | Ile | Gly | Tyr | Pro | Tyr | Ala | Val | Pro | Gly |
| | | | 290 | | | | | 295 | | | | | 300 | |
| GGT | AGA | TTC | AAT | GAA | TTA | TAT | GGT | TGG | GAC | TCC | TAT | ATG | ATG | GCA | 945
| Gly | Arg | Phe | Asn | Glu | Leu | Tyr | Gly | Trp | Asp | Ser | Tyr | Met | Met | Ala |
| | | | 305 | | | | | 310 | | | | | 315 | |
| CTA | GGT | CTC | CTA | GAA | GCC | AAC | AAG | ACT | GAT | GTT | GCA | AGA | GGT | ATG | 990
| Leu | Gly | Leu | Leu | Glu | Ala | Asn | Lys | Thr | Asp | Val | Ala | Arg | Gly | Met |
| | | | 320 | | | | | 325 | | | | | 330 | |
| GTG | GAG | CAT | TTT | ATT | TTT | GAG | ATT | AAT | CAC | TAT | GGA | AAA | ATA | TTG | 1035
| Val | Glu | His | Phe | Ile | Phe | Glu | Ile | Asn | His | Tyr | Gly | Lys | Ile | Leu |
| | | | 335 | | | | | 340 | | | | | 345 | |
| AAT | GCT | AAC | AGA | AGC | TAC | TAT | CTA | TGT | AGA | TCA | CAG | CCC | CCA | TTC | 1080
| Asn | Ala | Asn | Arg | Ser | Tyr | Tyr | Leu | Cys | Arg | Ser | Gln | Pro | Pro | Phe |
| | | | 350 | | | | | 355 | | | | | 360 | |
| TTG | ACT | GAA | ATG | GCC | TTG | GTA | GTA | TTC | AAA | AAA | CTT | GGT | GGT | AGG | 1125
| Leu | Thr | Glu | Met | Ala | Leu | Val | Val | Phe | Lys | Lys | Leu | Gly | Gly | Arg |
| | | | 365 | | | | | 370 | | | | | 375 | |
| AGT | AAT | CCC | GAT | GCT | GTG | GAT | TTG | TTG | AAA | AGA | GCT | TTC | CAA | GCA | 1170
| Ser | Asn | Pro | Asp | Ala | Val | Asp | Leu | Leu | Lys | Arg | Ala | Phe | Gln | Ala |
| | | | 380 | | | | | 385 | | | | | 390 | |

FIG. 3

| | | | | | | | | | | | | |
|---|---|---|---|---|---|---|---|---|---|---|---|---|
| AGC | ATA | AAA | GAG | TAC | AAA | ACT | GTT | TGG | ACC | GCA | TCT | CCA | AGG | CTT | 1215 |
| Ser | Ile | Lys | Glu | Tyr | Lys | Thr | Val | Trp | Thr | Ala | Ser | Pro | Arg | Leu | |
| | | | | 395 | | | | 400 | | | | | 405 | | |
| GAT | CCC | GAA | ACA | GGC | TTA | TCC | AGG | TAC | CAT | CCT | AAC | GGT | CTC | GGT | 1260 |
| Asp | Pro | Glu | Thr | Gly | Leu | Ser | Arg | Tyr | His | Pro | Asn | Gly | Leu | Gly | |
| | | | | 410 | | | | 415 | | | | | 420 | | |
| ATT | CCT | CCG | GAA | ACT | GAA | AGT | GAT | CAC | TTC | GAT | ACC | GTT | TTA | CTA | 1305 |
| Ile | Pro | Pro | Glu | Thr | Glu | Ser | Asp | His | Phe | Asp | Thr | Val | Leu | Leu | |
| | | | | 425 | | | | 430 | | | | | 435 | | |
| CCA | TAT | GCA | TCG | AAA | CAC | GGC | GTT | ACC | TTA | GAC | GAA | TTT | AAG | CAA | 1350 |
| Pro | Tyr | Ala | Ser | Lys | His | Gly | Val | Thr | Leu | Asp | Glu | Phe | Lys | Gln | |
| | | | | 440 | | | | 445 | | | | | 450 | | |
| CTT | TAT | AAC | GAT | GGT | AAG | ATA | AAG | GAG | CCT | AAA | TTG | GAT | GAG | TTT | 1395 |
| Leu | Tyr | Asn | Asp | Gly | Lys | Ile | Lys | Glu | Pro | Lys | Leu | Asp | Glu | Phe | |
| | | | | 455 | | | | 460 | | | | | 465 | | |
| TTT | CTT | CAT | GAC | CGT | GGC | GTT | AGA | GAA | TCT | GGA | CAC | GAC | ACT | ACA | 1440 |
| Phe | Leu | His | Asp | Arg | Gly | Val | Arg | Glu | Ser | Gly | His | Asp | Thr | Thr | |
| | | | | 470 | | | | 475 | | | | | 480 | | |
| TAT | AGG | TTT | GAG | GGC | GTA | TGT | GCC | TAC | CTG | GCC | ACT | ATT | GAC | CTG | 1485 |
| Tyr | Arg | Phe | Glu | Gly | Val | Cys | Ala | Tyr | Leu | Ala | Thr | Ile | Asp | Leu | |
| | | | | 485 | | | | 490 | | | | | 495 | | |
| AAT | TCT | CTT | CTT | TAC | AAA | TAC | GAG | ATT | GAT | ATT | GCG | GAC | TTC | ATA | 1530 |
| Asn | Ser | Leu | Leu | Tyr | Lys | Tyr | Glu | Ile | Asp | Ile | Ala | Asp | Phe | Ile | |
| | | | | 500 | | | | 505 | | | | | 510 | | |
| AAG | GAA | TTC | TGC | GAC | GAC | AAA | TAT | GAA | GAT | CCT | TTA | GAC | CAT | TCT | 1575 |
| Lys | Glu | Phe | Cys | Asp | Asp | Lys | Tyr | Glu | Asp | Pro | Leu | Asp | His | Ser | |
| | | | | 515 | | | | 520 | | | | | 525 | | |
| ATA | ACA | ACT | TCA | GCT | ATG | TGG | AAA | GAA | ATG | GCC | AAA | ATC | AGA | CAA | 1620 |
| Ile | Thr | Thr | Ser | Ala | Met | Trp | Lys | Glu | Met | Ala | Lys | Ile | Arg | Gln | |
| | | | | 530 | | | | 535 | | | | | 540 | | |
| GAA | AAG | ATT | ACC | AAA | TAT | ATG | TGG | GAT | GAC | GAG | TCG | GGG | TTT | TTC | 1665 |
| Glu | Lys | Ile | Thr | Lys | Tyr | Met | Trp | Asp | Asp | Glu | Ser | Gly | Phe | Phe | |
| | | | | 545 | | | | 550 | | | | | 555 | | |
| TTT | GAC | TAC | AAC | ACA | AAA | ATC | AAG | CAC | AGA | ACG | TCA | TAC | GAA | TCC | 1710 |
| Phe | Asp | Tyr | Asn | Thr | Lys | Ile | Lys | His | Arg | Thr | Ser | Tyr | Glu | Ser | |
| | | | | 560 | | | | 565 | | | | | 570 | | |
| GCA | ACT | ACA | TTC | TGG | GCA | TTA | TGG | GCT | GGA | CTT | GCC | ACG | AAG | GAG | 1755 |
| Ala | Thr | Thr | Phe | Trp | Ala | Leu | Trp | Ala | Gly | Leu | Ala | Thr | Lys | Glu | |
| | | | | 575 | | | | 580 | | | | | 585 | | |

FIG. 4

```
CAA GCA CAG AAA ATG GTG GAG AAA GCA CTA CCC AAG TTA GAG ATG    1800
Gln Ala Gln Lys Met Val Glu Lys Ala Leu Pro Lys Leu Glu Met
            590                 595                 600
CTT GGA GGT TTA GCT GCA TGT ACG GAG CGT TCT CGA GGC CCA ATT    1845
Leu Gly Gly Leu Ala Ala Cys Thr Glu Arg Ser Arg Gly Pro Ile
            605                 610                 615
TCT ATT TCG AGA CCA ATT AGA CAA TGG GAC TAT CCA TTT GGT TGG    1890
Ser Ile Ser Arg Pro Ile Arg Gln Trp Asp Tyr Pro Phe Gly Trp
            620                 625                 630
GCA CCC CAT CAA ATT CTT GCT TGG GAA GGC CTC CGT TCT TAT GGT    1935
Ala Pro His Gln Ile Leu Ala Trp Glu Gly Leu Arg Ser Tyr Gly
            635                 640                 645
TAT TTA ACT GTA ACG AAT AGG CTA GCT TAT AGA TGG CTT TTC ATG    1980
Tyr Leu Thr Val Thr Asn Arg Leu Ala Tyr Arg Trp Leu Phe Met
            650                 655                 660
ATG ACA AAG GCT TTT GTC GAT TAT AAT GGT ATT GTG GTT GAA AAA    2025
Met Thr Lys Ala Phe Val Asp Tyr Asn Gly Ile Val Val Glu Lys
            665                 670                 675
TAT GAT GTC ACA AGA GGA ACA GAT CCT CAT CGT GTT GAA GCA GAA    2070
Tyr Asp Val Thr Arg Gly Thr Asp Pro His Arg Val Glu Ala Glu
            680                 685                 690
TAC GGT AAT CAA GGT GCT GAC TTT AAA GGG GCA GCT ACT GAA GGT    2115
Tyr Gly Asn Gln Gly Ala Asp Phe Lys Gly Ala Ala Thr Glu Gly
            695                 700                 705
TTT GGA TGG GTC AAT GCC CGT TAC ATT CTT GGT TTG AAG TAT ATG    2160
Phe Gly Trp Val Asn Ala Arg Tyr Ile Leu Gly Leu Lys Tyr Met
            710                 715                 720
AAC AGT TAC GAA AGA AGA GAG ATT GGT GCT TGC ATT CCA CCA ATA    2205
Asn Ser Tyr Glu Arg Arg Glu Ile Gly Ala Cys Ile Pro Pro Ile
            725                 730                 735
TCA TTC TTT AGC AGT TTA AGG CCT CAA GAA AGA AAC CTC TAT GGA    2250
Ser Phe Phe Ser Ser Leu Arg Pro Gln Glu Arg Asn Leu Tyr Gly
            740                 745                 750
CTA TAG                                                        2256
Leu ***>
751
```

FIG. 5

| | | | | | | | | | | | | | |
|---|---|---|---|---|---|---|---|---|---|---|---|---|---|
| ATG | TCG | AAA | GCT | ACA | TAT | AAG | GAA | CGT | GCT | GCT | ACT | CAT | CCT | AGT | 45 |
| Met | Ser | Lys | Ala | Thr | Tyr | Lys | Glu | Arg | Ala | Ala | Thr | His | Pro | Ser |
| | | | | 5 | | | | 10 | | | | | 15 |

```
ATG TCG AAA GCT ACA TAT AAG GAA CGT GCT GCT ACT CAT CCT AGT    45
Met Ser Lys Ala Thr Tyr Lys Glu Arg Ala Ala Thr His Pro Ser
              5              10                  15
CCT GTT GCT GCC AAG CTA TTT AAT ATC ATG CAC GAA AAG CAA ACA    90
Pro Val Ala Ala Lys Leu Phe Asn Ile Met His Glu Lys Gln Thr
             20              25                  30
AAC TTG TGT GCT TCA TTG GAT GTT CGT ACC ACC AAG GAA TTA CTG   135
Asn Leu Cys Ala Ser Leu Asp Val Arg Thr Thr Lys Glu Leu Leu
             35              40                  45
GAG TTA GTT GAA GCA TTA GGT CCC AAA ATT TGT TTA CTA AAA ACA   180
Glu Leu Val Glu Ala Leu Gly Pro Lys Ile Cys Leu Leu Lys Thr
             50              55                  60
CAT GTG GAT ATC TTG ACT GAT TTT TCC ATG GAG GGC ACA GTT AAG   225
His Val Asp Ile Leu Thr Asp Phe Ser Met Glu Gly Thr Val Lys
             65              70                  75
CCG CTA AAG GCA TTA TCC GCC AAG TAC AAT TTT TTA CTC TTC GAA   270
Pro Leu Lys Ala Leu Ser Ala Lys Tyr Asn Phe Leu Leu Phe Glu
             80              85                  90
GAC AGA AAA TTT GCT GAC ATT GGT AAT ACA GTC AAA TTG CAG TAC   315
Asp Arg Lys Phe Ala Asp Ile Gly Asn Thr Val Lys Leu Gln Tyr
             95             100                 105
TCT GCG GGT GTA TAC AGA ATA GCA GAA TGG GCA GAC ATT ACG AAT   360
Ser Ala Gly Val Tyr Arg Ile Ala Glu Trp Ala Asp Ile Thr Asn
            110             115                 120
GCA CAC GGT GTG GTG GGC CCA GGT ATT GTT AGC GGT TTG AAG CAG   405
Ala His Gly Val Val Gly Pro Gly Ile Val Ser Gly Leu Lys Gln
            125             130                 135
GCG GCA GAA GAA GTA ACA AAG GAA CCT AGA GGC CTT TTG ATG TTA   450
Ala Ala Glu Glu Val Thr Lys Glu Pro Arg Gly Leu Leu Met Leu
            140             145                 160
GCA GAA TTG TCA TGC AAG GGC TCC CTA TCT ACT GGA GAA TAT ACT   495
Ala Glu Leu Ser Cys Lys Gly Ser Leu Ser Thr Gly Glu Tyr Thr
            165             170                 175
AAG GGT ACT GTT GAC ATT GCG AAG AGC GAC AAA GAT TTT GTT ATC   540
Lys Gly Thr Val Asp Ile Ala Lys Ser Asp Lys Asp Phe Val Ile
            180             185                 190
GGC TTT ATT GCT CAA AGA GAC ATG GGT GGA AGA GAT GAA GGT TAC   585
Gly Phe Ile Ala Gln Arg Asp Met Gly Gly Arg Asp Glu Gly Tyr
            195             200                 205
```

FIG. 6

```
GAT TGG TTG ATT ATG ACA CCC GGT GTG GGT TTA GAT GAC AAG GGA      630
Asp Trp Leu Ile Met Thr Pro Gly Val Gly Leu Asp Asp Lys Gly
            200             205             210
GAC GCA TTG GGT CAA CAG TAT AGA ACC GTG GAT GAT GTG GTC TCT      675
Asp Ala Leu Gly Gln Gln Tyr Arg Thr Val Asp Asp Val Val Ser
                215             220             225
ACA GGA TCT GAC ATT ATT ATT GTT GGA AGA GGA CTA TTT GCA AAG      720
Thr Gly Ser Asp Ile Ile Ile Val Gly Arg Gly Leu Phe Ala Lys
                    230             235             240
GGA AGG GAT GCT AAG GTA GAG GGT GAA CGT TAC AGA AAA GCA GGC      765
Gly Arg Asp Ala Lys Val Glu Gly Glu Arg Tyr Arg Lys Ala Gly
                245             250             255
TGG GAA GCA TAT TTG AGA AGA TGC GGC CAG CAA AAC TAA              804
Trp Glu Ala Tyr Leu Arg Arg Cys Gly Gln Gln Asn ***>
                260             265     267
```

FIG. 10
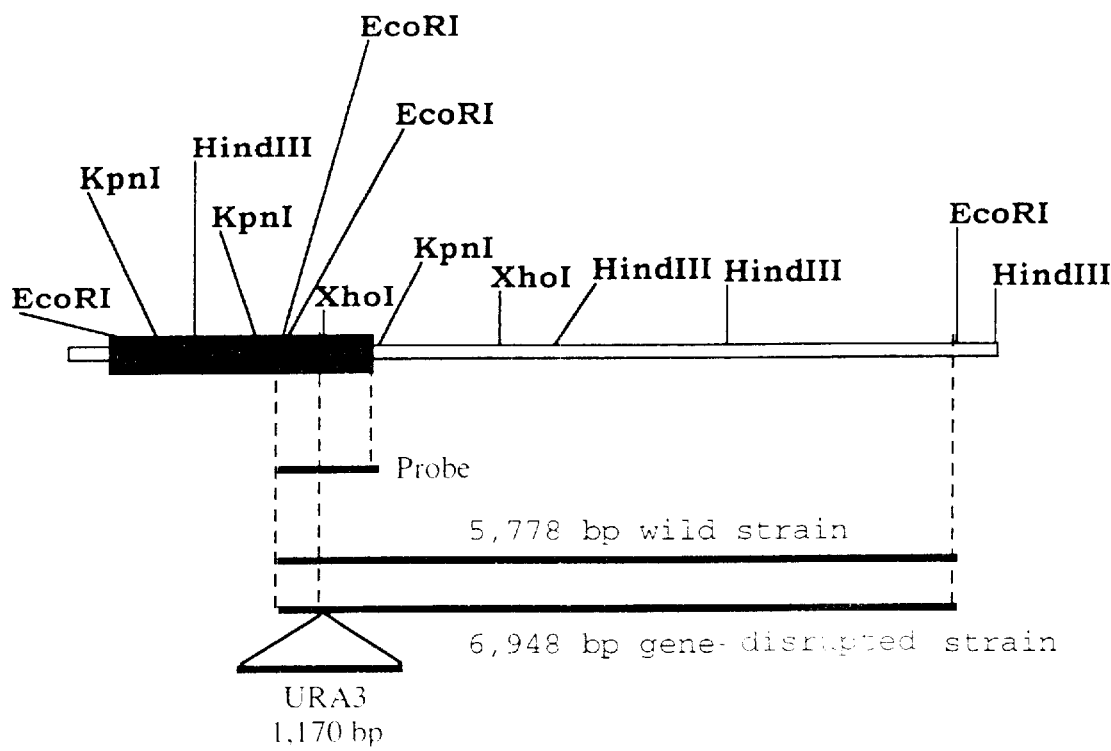
lane No.
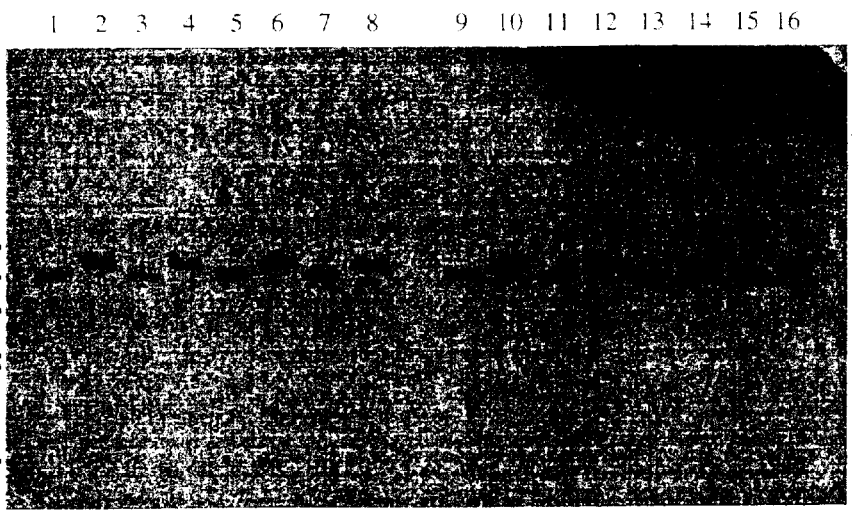

Fig. 11
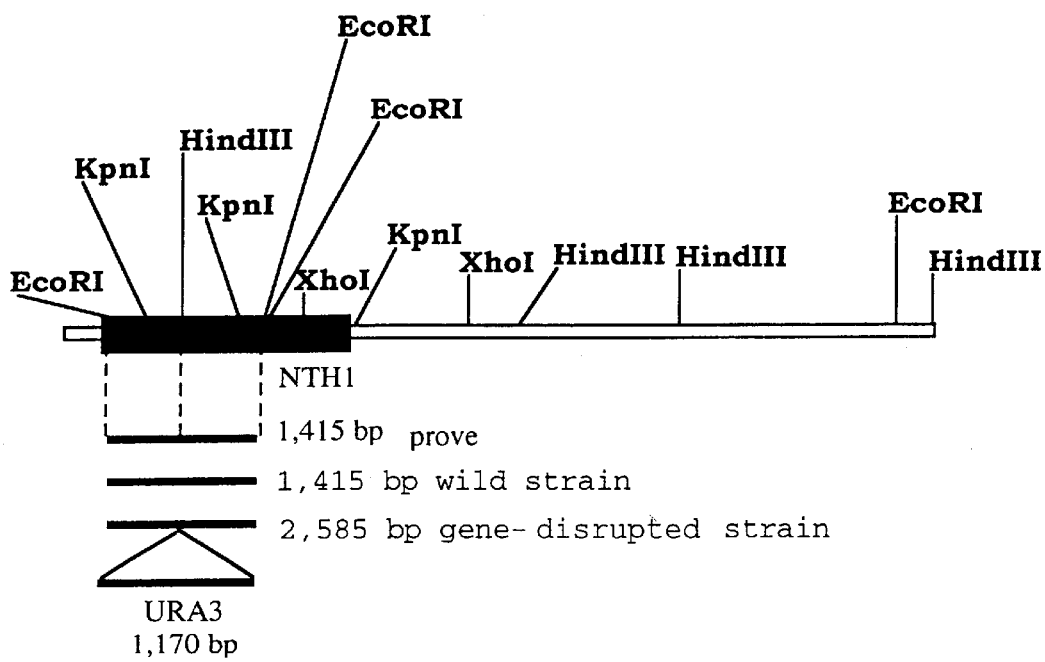
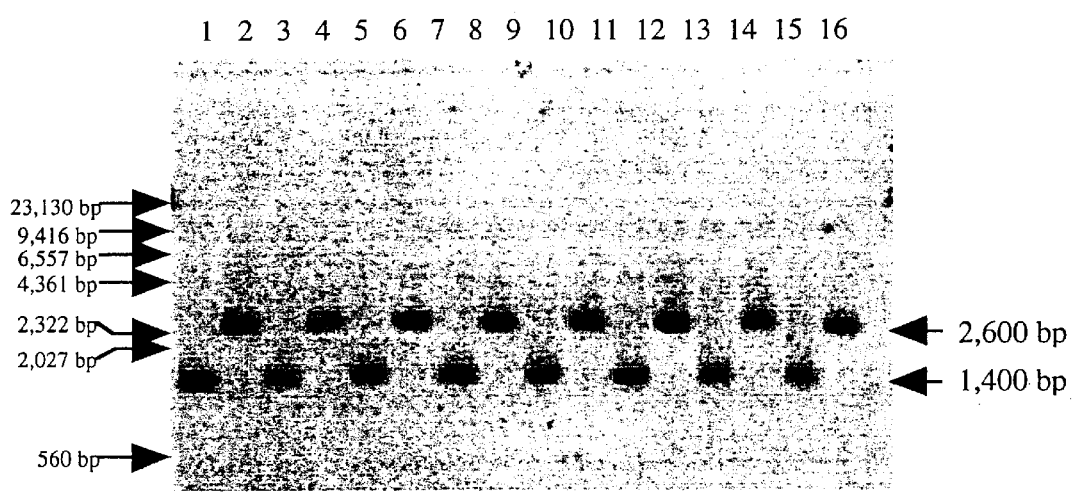

After having been incubated for 60 minutes, each dough was frozen and stored for 2 weeks, and then thawed. The amount of gaseous expansion of the thawed dough for 90 minutes was measured through fermography. Frozen dough test method II was employed.

FROZEN DOUGH-RESISTANT, PRACTICAL BAKER'S YEAST

DETAILED DESCRIPTION OF THE INVENTION

1. Technical Field of the Invention

The present invention relates to extremely excellent, frozen dough-resistant, practical baker's yeast.

Conventional frozen dough-resistant baker's yeast has heretofore been known, over which the frozen dough-resistant, practical baker's yeast of the invention is significantly excellent.

Frozen dough as produced through the process of preparing dough with the frozen dough-resistant baker's yeast of the invention followed by incubating and freezing it is resistant to long-term frozen storage of 2 weeks or longer, from which is produced good bread. The long-term stored, frozen dough gives, when thawed and baked, better bread than that from the frozen dough as prepared with the conventional frozen dough-resistant baker's yeast and stored long. Specifically, in the invention in which the NTH1 gene in practical baker's yeast having various excellent characteristics but not having resistance to frozen dough is inactivated, it has become possible to make the practical baker's yeast have frozen dough resistance that is comparable to or higher than that of ordinary commercially-available, frozen dough-resistant baker's yeast.

Therefore, the frozen dough-resistant, practical baker's yeast of the invention greatly contributes to developments in the frozen dough industry.

2. Prior Art (Accumulation of Trehalose)

Regarding the frozen dough resistance of yeast, a technique of gene manipulation to ensure the accumulation of trehalose in yeast was reported by Helmut Holzer et al. of the Freiburg University (see J.B.C., Vol. 268, No. 7, 1993).

In their report, the NTH1 gene (neutral trehalase gene) of yeast was cloned, and then URA3 (uridylic acid synthetase gene) was introduced into a-type and α-type NTH1 genes to thereby disrupt the NTH1 gene in the yeast. Through their technique reported, they confirmed the increase in the accumulation of trehalose in the yeast with no decomposition of trehalose therein.

On the other hand, Johan M. Thevelein et al. inserted LEU2 into the NTH1 gene of α-type and a/α-type yeasts to thereby disrupt the NTH1 gene therein, and confirmed the accumulation of trehalose in the resulting yeasts (see Applied and Environmental Microbiology, Vol. 61, No. 1, January 1995, pp. 105–115).

However, they concluded that their technique is ineffective in producing frozen dough-resistant baker's yeast.

As above, it is known to disrupt the NTH1 gene of a-type, α-type and a/α-type yeasts with URA3 to thereby increase the amount of trehalose to be accumulated in those yeasts.

(Hybridization of Yeast)

In general, baker's yeast includes haploids (a-type and α-type), diploids (a/α-type, a/a-type, a /α-type), triploids (diploid x a-type or α-type), tetraploids (diploid x diploid), etc. At present, in Japan, almost all commercially-available baker's yeasts are a/α-type diploids.

For obtaining excellent diploid baker's yeast, two methods are known. One is to obtain a variety of mutants from original diploid yeast strain by spontaneous, or mitogen induced mutagenesis, and to screen them to select mutants with good properties; and the other is to mate haploid a-type yeast with good properties and a haploid α-type yeasts with good properties respectively, and to screen the resulting diploid yeasts to select hybrids with good properties.

To mate them, an a-type yeast and an α-type yeast of the same amount are mixed and cultivated together, whereupon in about 12 hours after conjugation of the two in which are formed hybrids. This technique is already known.

PROBLEMS TO BE SOLVED BY THE INVENTION

The conventional gene manipulation of disrupting the NTH1 gene (neutral trehalase gene) in yeast may produce the increase in the amount of trehalose to be accumulated in the resulting yeast, but frozen dough-resistant, practical baker's yeast capable of finally giving delicious bread could not be obtained as yet. Given this situation, the object of the invention is to construct frozen dough-resistant, practical baker's yeast capable of finally giving delicious bread, to produce excellent frozen dough, and to produce delicious bread by thawing, fermenting and baking the frozen dough.

MEANS FOR SOLVING THE PROBLEMS

Even though freezing-resistant yeast could be constructed through NTH1 gene disruption, frozen dough-resistant, practical baker's yeast could not be obtained as yet. We, the present inventors desired to modify practical baker's yeast having excellent properties but not having resistance to frozen dough into frozen dough-resistant, practical baker's yeast still having its original excellent properties and additionally having frozen dough resistance that is comparable to or higher than that of ordinary, commercially-available freezing-resistant yeast. For this purpose, we analyzed in detail starting yeast strains, frozen dough and even final bread in various experiments and, as a result, have completed the invention.

The invention relates to a set of NTH1 gene-disrupted, haploid yeasts as produced through gene manipulation of disrupting the NTH1 gene in a set of haploid yeasts of which the original hybridized diploid is practical baker's yeast.

The invention also relates to a diploid or higher polyploid, frozen dough-resistant, practical baker's yeast as produced through mating with one or more NTH1 gene-disrupted, haploid yeasts produced through gene manipulation of disrupting the NTH1 gene in a haploid yeast of which the diploid is practical baker's yeast. Where two or more yeasts are used in that mating, at least one of those is the NTH1 gene-disrupted, haploid yeast while the others may be yeasts with no gene disruption.

The invention further relates to frozen dough-resistant, practical baker's yeast-containing, frozen dough, as produced by preparing dough with a diploid or higher polyploid, frozen dough-resistant, practical baker's yeast that is produced through mating with one or more NTH1 gene-disrupted, haploid yeasts produced through gene manipulation of disrupting the NTH1 gene in a haploid yeast of which the diploid is practical baker's yeast, then incubating it and thereafter freezing it. Optionally in the invention, the frozen dough is thawed, fermented and baked to give delicious bread.

BRIEF DESCRIPTION OF THE DRAWINGS

FIG. 1 shows the starting part of the gene sequence of NTH1 gene (SEQ ID NO: 1).

FIG. 2 shows the part of the gene sequence of NTH1 gene that follows FIG. 1 (SEQ ID NO: 1).

FIG. 3 shows the part of the gene sequence of NTH1 gene that follows FIG. 2 (SEQ ID NO: 1).

FIG. 4 shows the last part of the gene sequence of NTH1 gene (SEQ ID NO: 1).

FIG. 5 shows the former half of the gene sequence of URA3 (SEQ ID NO: 3).

FIG. 6 shows the latter half of the gene sequence of URA3 (SEQ ID NO:3).

FIG. 10 shows the confirmation of the disruption of NTH1 gene with pNTHd1.

FIG. 11 shows the confirmation of the disruption of NTH1 gene with pNTHd2.

Figure 7:
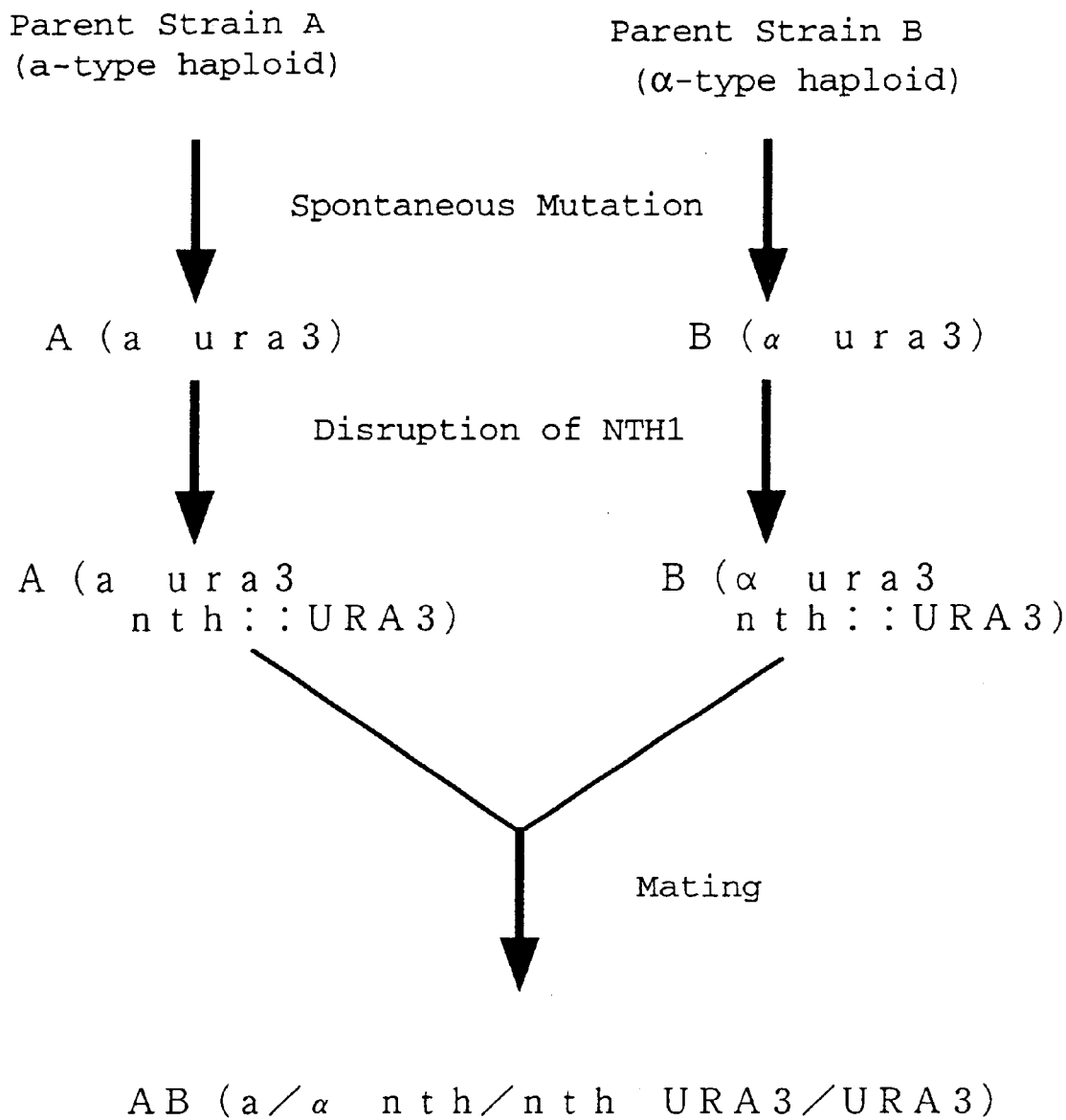
FIG. 7 shows a process of constructing a hybrid.

MODES OF CARRYING OUT THE INVENTION
(Screening for Haploid Yeasts of which the Diploids are Practical Baker's Yeasts)

In the invention, the screening of yeast strains for those to be subjected to gene manipulation is indispensable.

First are selected haploid yeast strains, which must be identified as to whether they are a-type ones or α-type ones.

Where a selected haploid yeast could be conjugated with a previously prepared α-type haploid yeast in the culture of the two in a ratio of 1/1, the haploid yeast is identified as an a-type one. On the other hand, where a selected haploid yeast could be conjugated with a previously prepared a-type haploid yeast in the culture of the two in a ratio of 1/1, the haploid yeast is identified as an α-type one.

An a-type or α-type haploid yeast may be mated with an α-type or a-type haploid to construct an a/α-type diploid yeast, which is then mass-cultivated. Using the thus-cultivated yeasts, various bread samples are prepared, from which are selected excellent bread samples. The yeasts used in preparing the excellent bread samples are known, and they are determined to be haploid yeasts to be subjected to gene manipulation.

There are various types of bread, including, for example, loaves, rolls, croissants, French bread and rolls, and buns, for all of which diploid yeasts as constructed from various haploid yeasts are tested.

Depending on the type of the haploid yeasts to be mated, as to whether they are a-type ones or α-type ones, the characteristics of the bread to be prepared by baking frozen dough that comprises the mated diploid yeast greatly vary. Therefore, the screening of the suitable haploid yeast to be subjected to gene manipulation is extremely difficult. However, in order to obtain the intended, frozen dough-resistant, practical baker's yeast, this screening step is indispensable.

(Disruption of NTH1 Gene)

In the invention, where a marker gene, such as URA3 (uridylic acid synthetase) (Gene 29: 113–124, (1984)), which is shown in FIG. 5 and FIG. 6, or ADE2 or LYS2, is inserted into the NTH1 gene (neutral trehalase gene) (J.B.C. 268: 4766–4774 (1993)) of a haploid yeast, which is shown in FIG. 1, FIG. 2, FIG. 3 and FIG. 4, the NTH1 gene is disrupted and could no more be expressed in the yeast. In the resulting yeast with the NTH1 gene disrupted, the URA3 or other auxotrophic marker gene as inserted into the yeast is expressed, whereby the disruption of the NTH1 gene in the yeast is confirmed. The URA3 and other marker genes to be inserted into the yeast are preferably those derived from *Saccharomyces cerevisiae*, especially those from baker's yeast, for realizing their self-cloning.

(Confirmation of URA3)

1. Construction of URA3 strain

To introduce a gene marker, ura3 (URA3-defective strain) into a haploid strain, cells of the strain are screened in a 5-fluoro-orotic acid-containing medium. Briefly, cells of a haploid strain are cultivated in an YPD liquid medium, centrifuged, and washed with a sterilized physiological saline solution. About $10^8$ cells thus cultivated are applied onto a 5-fluoro-orotic acid-containing medium (0.7% YEAST NITROGEN BASE (DIFCO), 2% glucose, 0.1% 5-fluoro-orotic acid, 0.05% uracil, 2% agar) and cultivated thereon, and the cells growing on the medium to give colonies thereon are selected. The cells having grown on the medium do not have intact URA3 gene, as having been spontaneously mutated. Such URA3-defective cells are obtained at a frequency of one cell per $10^6$ to $10^7$ cells.

2. Confirmation of URA3

Those URA3-defective cells could not grow on an uracil-free medium, but could grow thereon only after having been transformed with an URA3-containing plasmid, such as YCp50 or the like. Therefore, through the transformation of those cells, the defect of URA3 therein can be confirmed.

The object of the disruption of the NTH1 gene in haploid yeasts is to prevent the NTH1 gene from being expressed in the yeasts to give a neutral trehalase which decomposes trehalose. For this, therefore, all or a part of the gene sequence of the NTH1 gene is deleted.

Preferably, in the invention, URA3 is inserted entirely or partly into the region of the NTH1 gene of a haploid yeast to thereby disrupt the NTH1 gene therein.

First, a part of the gene sequence of the NTH1 gene shown in FIG. 1, FIG. 2, FIG. 3 and FIG. 4 is inserted into an *E. coli* vector, such as pUC19, then the URA3 gene shown in FIG. 5 and FIG. 6 is inserted into the partial region of the NTH1 gene in the vector. The resulting plasmid is proliferated in *E. coli* cells. From this plasmid, cleaved out is only the DNA fragment of NTH1 gene (former half)—URA3—NTH1 gene (latter half). With the thus-isolated DNA fragment, is thereafter transformed a haploid yeast, of which the diploid is a practical baker's yeast, by a lithium acetate method.

The DNA fragment, NTH1 gene (former half)—URA3 —NTH1 gene (latter half) in the yeast is bonded and recombined whereby the NTH1 gene is completely divided into two, its former half and latter half, via URA3 therebetween, resulting in that the gene is disrupted.
(Mating of NTH1 Gene-disrupted Haploid Yeast)

The NTH1 gene-disrupted haploid yeast obtained herein is either an a-type or α-type one, while having such necessary properties that its diploid yeast can be a practical baker's yeast. In other words, only the NTH1 gene is disrupted in the haploid yeast through the gene disruption, while the other genes in the resulting NTH1 gene-disrupted haploid yeast are not changed at all and still maintain their intrinsic properties.

One or more NTH1 gene-disrupted haploid yeasts as prepared through the process of disrupting the NTH1 gene of a haploid yeast, of which the diploid is a practical baker's yeast, are mated with any other haploid yeasts to give diploid or higher polyploid, frozen dough-resistant, practical baker's yeasts.

One preferred embodiment of the mating is to mate an a-type, NTH1 gene-disrupted haploid yeast is mated with an α-type, NTH1 gene-disrupted haploid yeast to give a diploid yeast.

FIG. 7 shows an outline of the process of producing the diploid, frozen dough-resistant, practical baker's yeast of the invention.

Two of many diploid, frozen dough-resistant, practical baker's yeasts obtained herein, a baker's yeast of *Saccharomyces cerevisiae* T154 (FERM BP-5678) and a baker's yeast of *Saccharomyces cerevisiae* T207 (FERM BP-5679), were deposited on Sep. 26, 1996 in the National Institute of Advanced Industrial Science and Technology, Agency of Industrial Science and Technology of AIST Tsukuba Central 6, 1-1-1 Higashi, Tsukuba, Ibaraki, Japan (the old name and address: National Institute of Bioscience and Human-Technology, Agency of Industrial Science and Technology, Ministry of International Trade and Industry, 1-3, Higashi 1-chome, Tsukuba-shi, Ibaraki-ken 305, Japan).

The anti-freezing property of the polyploid, frozen dough-resistant, practical baker's yeast of the invention is extremely excellent, especially in frozen dough as prepared by incubating dough and then freezing it.

The production of bread from frozen dough has derived from the need for the improvement in the working conditions in bakeries. As is known from the distributive machinery for frozen dough products, dough is frozen not directly but after having been incubated for about 60 minutes (this period is from the mixing of dough materials to the freezing of the resulting dough, for which the dough is substantially incubated), and thereafter the thus-expanded dough is frozen as it is. Then, the frozen dough products are delivered to bakeries, in which they are stored for a while, and thereafter thawed, fermented (proofing) and baked depending on the working time.

In view of the distributive machinery for frozen dough products in the market, the baker's yeast to be used in the frozen dough must have good and long-lasting freezing resistance in the incubated and frozen dough.

The polyploid, frozen dough-resistant, practical baker's yeast of the invention is well resistant even to incubated dough in the frozen condition. When the frozen dough comprising the yeast of the invention is thawed and fermented, the yeast well exhibits its capacity, and the bread to be obtained by baking the thus-fermented dough is tasty and delicious.

EXAMPLES

Example 1

(Haploid Yeast of which the Diploid is Practical Baker's Yeast)

25 stock cultures of wild haploid yeasts were identified as to whether they are a-type ones or α-type ones, and all of these were tested to know as to whether or not their diploids could be practical baker's yeasts. As a result of the test, 8 strains as in Table 1 were selected.

These 8 strains were subjected to gene disruption according to the method mentioned below, by which the NTH1 gene existing therein was disrupted. Before and after the gene disruption, the neutral trehalase activity of each strain was measured.

The data obtained are shown in Table 1, from which it was confirmed that the neutral trehalase activity of the NTH1 gene-disrupted strains was significantly lowered. That data indicate the disruption of the NTH1 gene in those stains.

TABLE 1

Comparison between the NTH activity of haploid yeast strain (wild strain), of which the diploid is practical baker's yeast, and that of NTH1 gene-disrupted strain

| Strain No., and its | NTH (spec. act, (mU/mg protein)) | |
|---|---|---|
| type | Wild | Δnth |
| 2 (a) | 93 | 4 |
| 7 (a) | 87 | 6 |
| 12 (α) | 83 | 3 |
| 13 (α) | 12 | 0 |
| 14 (a) | 64 | 3 |
| 18 (α) | 75 | 1 |
| 19 (α) | 39 | 1 |
| 21 (a) | 18 | 0 |

NTH1 Gene to be Disrupted)

It is known that NTH1 gene is positioned just adjacent to the centromere in the fourth chromosome of *Saccharomyces cerevisiae* of baker's yeast, and its gene sequence is as in FIG. 1, FIG. 2, FIG. 3 and FIG. 4.

Figure 8:
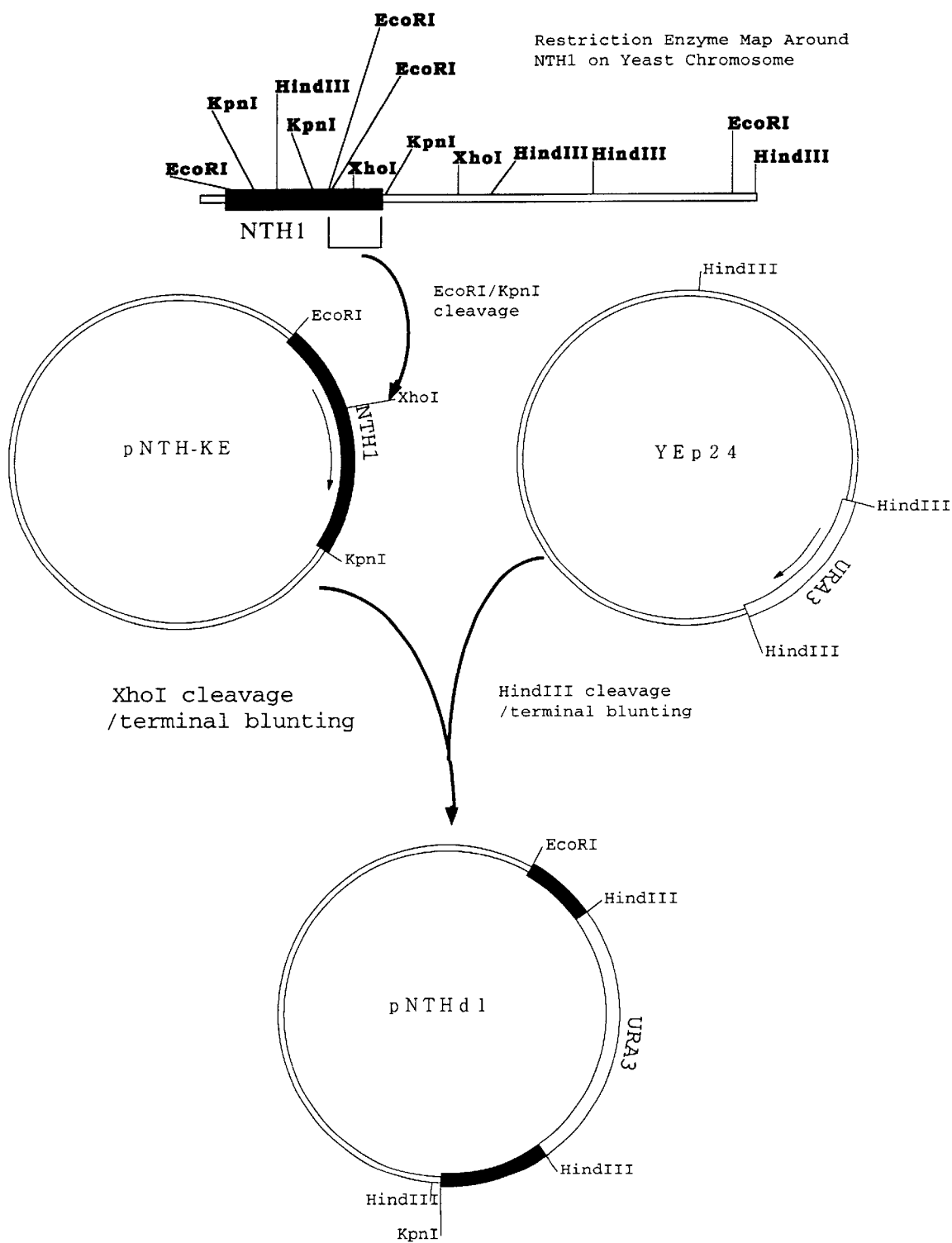
FIG. 8 shows the construction of pNTHd1.

In the invention, the NTH1 gene of baker's yeast was obtained from the region containing the centromere in the fourth chromosome of a usually-available yeast vector, YCp50 through gene eviction, and its sequence was confirmed as in FIG. 1, FIG. 2, FIG. 3 and FIG. 4.
(Construction of Vector for Disrupting NTH1 Gene)
1. pNTHd1:

From the NTH1 gene cloned, pNTHd1 was constructed as in FIG. 8.

Precisely, the region of NTH1 gene between KpnI-recgnition site in the 3'-side and EcoRI-recgnition site in the upstream site above it, which was about 770 bp, was cleaved at the both recognition sites, as in FIG. 8, and the resulting fragment was inserted into a commercially-available E. coli vector, pUC19, at the same restriction enzyme-recognition sites (KpnI and EcoRI-recognition sites) to obtain pNTH-KE.

The resulting plasmid was cleaved at the XhoI-recognition site, and its terminals were blunted with a DNA polymerase. On the other hand, the URA3 gene in commercially-available YEp24, which is as in FIG. 8, was cleaved with HindIII and recovered. This URA3 fragment of about 1,170 bp was blunted with a DNA polymerase, and inserted into the XhoI-cleaved site of blunted as above the plasmid pNTH-KE through ligation with a ligase to obtain pNTHd1.

Figure 9:
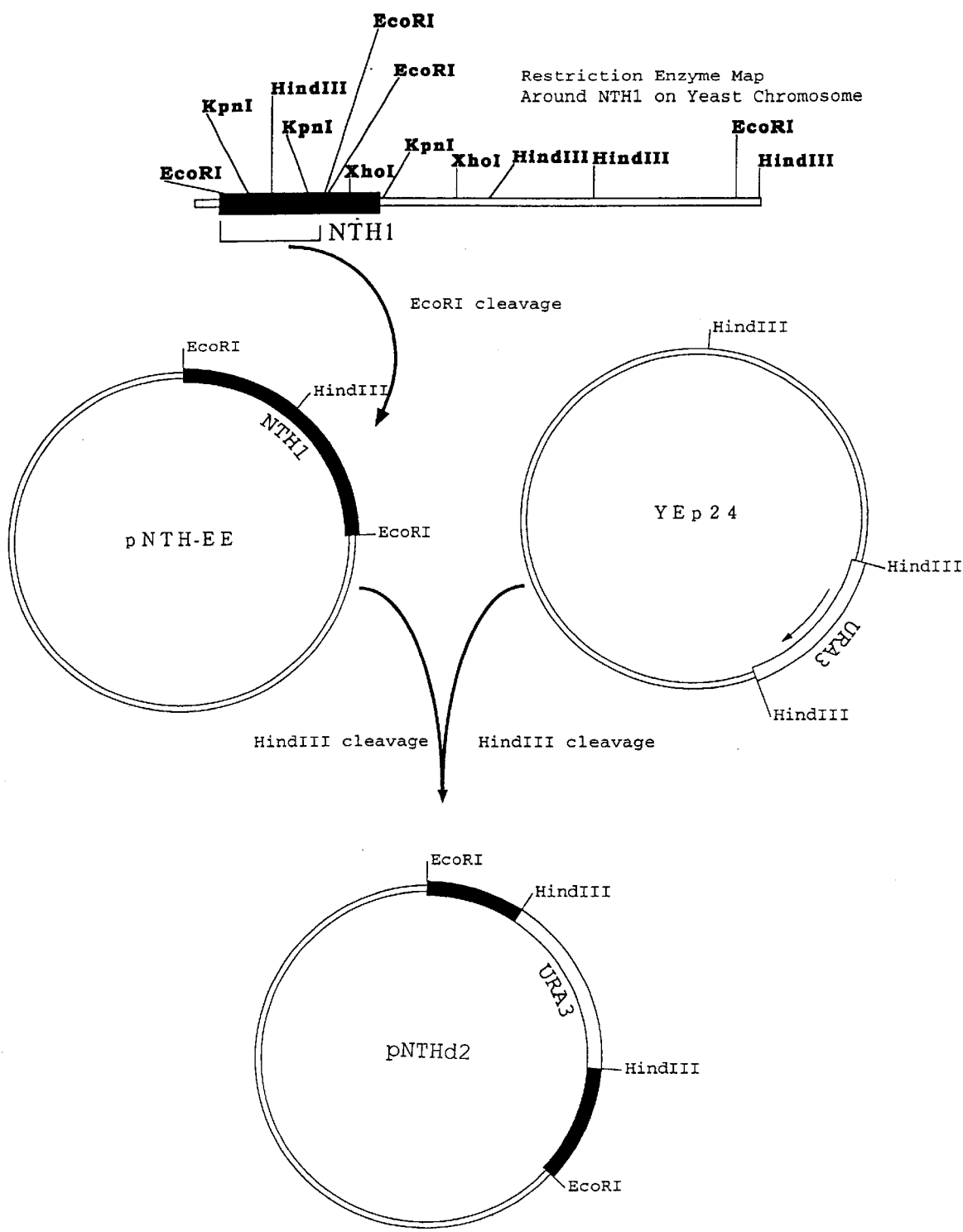
FIG. 9 shows the construction of pNTHd2.

2. pNTHd2:

From the NTH1 gene cloned, pNTHd2 was constructed as in FIG. 9.

Precisely, the region of EcoRI-EcoRI fragment of about 1,420 bp in the 5'-side of NTH1 gene was cleaved, as in FIG. 9, and the resulting fragment was inserted into a E. coli vector, pBR322dH (this was prepared by cleaving commercially-available E. coli vector, pBR322 with HindIII, blunting the terminals with a DNA polymerase, and re-cyclizing the resulting fragment with a ligase) at the EcoRI-recognition site to obtain pNTH-EE.

The resulting plasmid was cleaved at the HindIII-recognition site. On the other hand, the URA3 gene in commercially-available YEp24, which is as in FIG. 5 and FIG. 6, was cleaved with HindIII. The resulting URA3 fragment of about 1,170 bp was inserted into the plasmid pNTH-EE, using a ligase, to obtain pNTHd2.

(Disruption of NTH1 Gene of Haploid Yeast)

1. Disruption of NTH1 gene with pNTHd1:

pNTHd1 was cleaved with EcoRI and KpnI to isolate a DNA fragment of NTH1 gene (former half)—URA3—NTH1 gene (latter half), with which each haploid yeast of No. 2, No. 7, No. 12, No. 13, No. 14, No. 18, No. 19 and No. 21, all shown in Table 1, was transformed in a lithium acetate process.

The chromosomal DNA extracted from each of those transformant strains was digested with EcoRI, and 0.5 μg of the DNA fragment was subjected to agarose gel electrophoresis followed by Southern hybridization, from which was confirmed the gene disruption as in FIG. 10. In FIG. 10, the left side column indicates the position of the bands of the molecular weight markers (λDNA-HindIII digested). Each lane corresponds to the strain number as follows: Lane 1 is No. 2; lane 2 is No. 2d-1; lane 3 is No. 7; lane 4 is No. 7d-1; lane 5 is No. 12; lane 6 is No. 12d-1; lane 7 is No. 13; lane 8 is No. 13d-1; lane 9 is No. 14; lane 10 is No. 14d-1; lane 11 is No. 18; lane 12 is No. 18d-1; lane 13 is No. 19; lane 14 is No. 19d-1; lane 15 is No. 21; and lane 16 is No. 21d-1. In those, "d-1" means that the strain was processed with pNTHd1 for gene disruption, and the same shall apply to the strains in Table 2. The data in FIG. 10 verify the disruption of the NTH1 gene in those strains.

2. Disruption of NTH1 gene with pNTHd2:

pNTHd2 was cleaved with EcoRI to isolate a DNA fragment of NTH1 gene (former half) -URA3 -NTH1 gene (latter half), with which each haploid yeast of No. 2, No. 7, No. 12, No. 13, No. 14, No. 18, No. 19 and No. 21, all shown in Table 1, was transformed in a lithium acetate method.

The chromosomal DNA as extracted from each of those transformant strains was decomposed with RcoRI, and 0.5 μg of the DNA fragment was subjected to agarose gel electrophoresis followed by Southern hybridization, from which was confirmed the gene disruption as in FIG. 11. In FIG. 11, the left side column indicates the position of the bands of the molecular weight markers (λDNA-HindIII decomposed). Each lane corresponds to the strain number as follows: Lane 1 is No. 2; lane 2 is No. T2d-2; lane 3 is No. 7; lane 4 is No. T7d-2; lane 5 is No. 12; lane 6 is No. T12d-2; lane 7 is No. 13; lane 8 is No. T13d-2; lane 9 is No. 14; lane 10 is No. T14d-2; lane 11 is No. 18; lane 12 is No. T18d-2; lane 13 is No. 19; lane 14 is No. T19d-2; lane 15 is No. 21; and lane 16 is No. T21d-2. In those, "T d-2" means that the strain was processed with pNTHd2 for gene disruption, and the same shall apply to the strains in Table 3. The data in FIG. 11 verify the disruption of the NTH1 gene in those strains.

Example 2
(Mating of a-type Haploid Yeast and α-type Haploid Yeast)
1. The mating matrix I in Table 2 shows various combinations of wild strain and pNTHd1-processed strain.

TABLE 2

| | Mating Matrix I | | | | | | | |
|---|---|---|---|---|---|---|---|---|
| | 2 (a) | 7 (a) | 14 (a) | 21 (a) | 2d-1 (a) | 7d-1 (a) | 14d-1 (a) | 21d-1 (a) |
| 12 (α) | T101 | T102 | 1103 | T104 | T105 | T106 | T107 | T108 |
| 13 (α) | T109 | T110 | T111 | T112 | T113 | T114 | T115 | T116 |
| 18 (α) | T117 | T118 | T119 | T120 | T121 | T122 | T123 | T124 |
| 19 (α) | T125 | T126 | T127 | T128 | T129 | T130 | T131 | T132 |
| 12d-1 (α) | T133 | T134 | T135 | T136 | T137 | T138 | T139 | T140 |
| 13d-1 (α) | T141 | T142 | T143 | T144 | T145 | T146 | T147 | T148 |
| 18d-1 (α) | T149 | T150 | T151 | T152 | T153 | T154 | T155 | T156 |
| 19d-1 (α) | T157 | T158 | T159 | T160 | T161 | T162 | T163 | T164 |

In Table 2, the strains in the uppermost row are all a-type ones, while those in the leftmost column are all α-type ones. In this, the strains with "d-1" are gene-disrupted ones as processed with pNTHd1; while those with no "d-1" are wild strains as in Table 1.

Each one in the uppermost row was mated with each one in the leftmost column to obtain 64 diploid yeasts, T101 through T164, in all as in Table 2.

The mating was effected as follows: First, a pair of a-type strain and α-type strain were separately cultivated and proliferated in YPD media at 30° C. for one day. The number of the thus-proliferated cells of the both strains was nearly the same. The cells of the both strains were put into a fresh YPD medium and further cultivated therein at 30° C. for 12 hours. Then, the conjugated yeast cells were isolated, applied onto an YPD-agar medium, and cultivated thereon at 30° C. for one day. Relatively large colonies formed were taken out. It was confirmed that the cells in those colonies have no conjugating ability and that they are larger than the haploid cells through microscopic observation. Thus, the formation of diploid yeast cells was confirmed.

2. The mating matrix II in Table 3 shows various combinations of pNTHd2-processed strains.

TABLE 3

Mating Matrix II

|  | T12d-2 (α) | T13d-2 (α) | T18d-2 (α) | T19d-2 (α) |
|---|---|---|---|---|
| T2d-2 (a) | T201 | T202 | T203 | T204 |
| T7d-2 (a) | T205 | T206 | T207 | T208 |
| T14d-2 (a) | T209 | T210 | T211 | T212 |
| T21d-2 (a) | T213 | T214 | T215 | T216 |

In Table 3, the strains both in the uppermost row and in the leftmost column are all gene-disrupted ones as processed with pNTHd2. In this, the strains in the uppermost row are α-type ones, while those in the leftmost column are a-type ones.

Each one in the uppermost row was mated with each one in the leftmost column to obtain 16 diploid yeasts, T201 through T216, in all as in Table 3.

The mating was effected in the same manner as in 1.
(Deposition of Yeast Strains)

T154 in Table 2, *Saccharomyces cerevisiae* T154 (FERM BP-5678), and T207 in Table 3, *Saccharomyces cerevisiae* T207 (FERM BP-5679) were deposited on Sep. 26, 1996 in the National Institute of Bioscience and Human-Technology, Agency of Industrial Science and Technology of Japan.

Example 3
(Cultivation of Diploid, Frozen Dough-resistant, Practical Baker's Yeast)

Many diploid, frozen dough-resistant, practical baker's yeasts obtained in Example 2 as in Table 2 and Table 3 were cultivated. For those, employed was industrial fed bach culture (fed bach culture) in which was used molasses as the carbon source. Briefly, the yeasts were cultivated in mini-jar fermenters (volume: 3 liters) and 30-liter jar fermenters according to conventional feeding culture.
(Medium Composition)

|  | Seed Culture | Main Culture |
|---|---|---|
| Mini-jar culture |  |  |
| Saccharide (in terms of sucrose) | 91.5 g | 140 g |
| Urea | 9.2 g | 14 g |
| Monosodium phosphate dihydrate | 1.8 g | 2.8 g |
| Seed yeast (wet) | 10 g (*1) | 50 g (*2) |
| Mini-jar |  |  |
| Maker: Oriental Bioservice KK |  |  |
| Name: Laboratory Fermenter LS-3Z |  |  |
| Volume: 3 liters |  |  |
| Revolution of stirrer: 600 rpm |  |  |
| Aeration: 2 liters/min |  |  |
| 30-Liter jar culture |  |  |
| Saccharide (in terms of sucrose) | 1035 g | 1400 g |
| Urea | 103 g | 140 g |
| Monosodium phosphate dihydrate | 20.7 g | 28 g |
| Seed yeast (wet) | 20 g (*1) | 420 g (*2) |

-continued

|  | Seed Culture | Main Culture |
|---|---|---|
| 30-Liter jar |  |  |
| Maker: Oriental Bioservice KK |  |  |
| Name: Fermenter Control System MC-10 |  |  |
| Volume: 30 liters |  |  |
| Revolution of stirrer: 600 rpm |  |  |
| Aeration: 16 liters/min |  |  |

*1 One platinum loop of yeast cells was planted in a 1-liter Sakaguchi flask charged with 250 ml of an YPD medium, and cultivated therein at 30° C. for 2 days. The cells of two flasks were used as the seed cells in the mini-jar, while those of four flasks in the 30-liter jar.
*2 The cells grown in the seed culture were taken out through centrifugation, and washed with deionized water. A part of those cells were used.

A part of those cells were used.

All the tested strains gave an yield of from 120 to 140%, relative to the saccharide used, of the yield given by the commercially-available baker's yeast strain as cultivated in the same manner. The data verify that those strains can be cultivated on industrial scale.

Example 4
(Frozen Dough-resistant, Practical Baker's Yeast-containing Frozen Dough)

The cultivated yeasts as obtained in the above each were compressed into solid, like commercially-available yeast. This was added to dough having the composition mentioned below, and mixed.

|  | Sugarless Dough | Low-sugar Dough (for loaves) |
|---|---|---|
| Wheat flour | 100 g | 100 g |
| Sugar | 0 g | 6 g |
| Salt | 2 g | 2 g |
| Yeast | 2 g | 2 g |
| Water | 65 ml | 65 ml |

After having been mixed, the dough was divided into 40 g pieces, incubated at 30° C., degassing, then frozen and stored at −20° C. Thus were obtained frozen dough-resistant, practical baker's yeast-containing frozen dough samples.
(Gas Production of Frozen Dough)

Frozen dough-resistant, practical baker's yeasts, T118 and T154 in Table 2, and commercially-available baker's yeast (manufactured by Oriental Yeast Industry Co.) were used in preparing frozen dough samples. The samples were tested in accordance with the baker's yeast test method of the Yeast Industry Association of Japan.

|  | Sugarless Dough | Low-sugar Dough (for loaves) | High-sugar Dough |
|---|---|---|---|
| Wheat flour | 100 g | 100 g | 100 g |
| Sugar | 0 g | 5 g | 30 g |
| Salt | 2 g | 2 g | 0.5 g |
| Yeast | 4 g | 4 g | 6 g |
| Water | 65 ml | 65 ml | 52 ml |

Each yeast was added to the dough having any of the above-mentioned compositions, mixed, and divided into plural portions each having a wheat flour content of 30 g. These were incubated at 30° C. for 60 minutes, shaped, then frozen and stored for 2 weeks, and thereafter thawed, whereupon the gaseous volume of each sample as thawed and kept at 30° C. for 90 minutes was measured through fermography.

Figure 12:
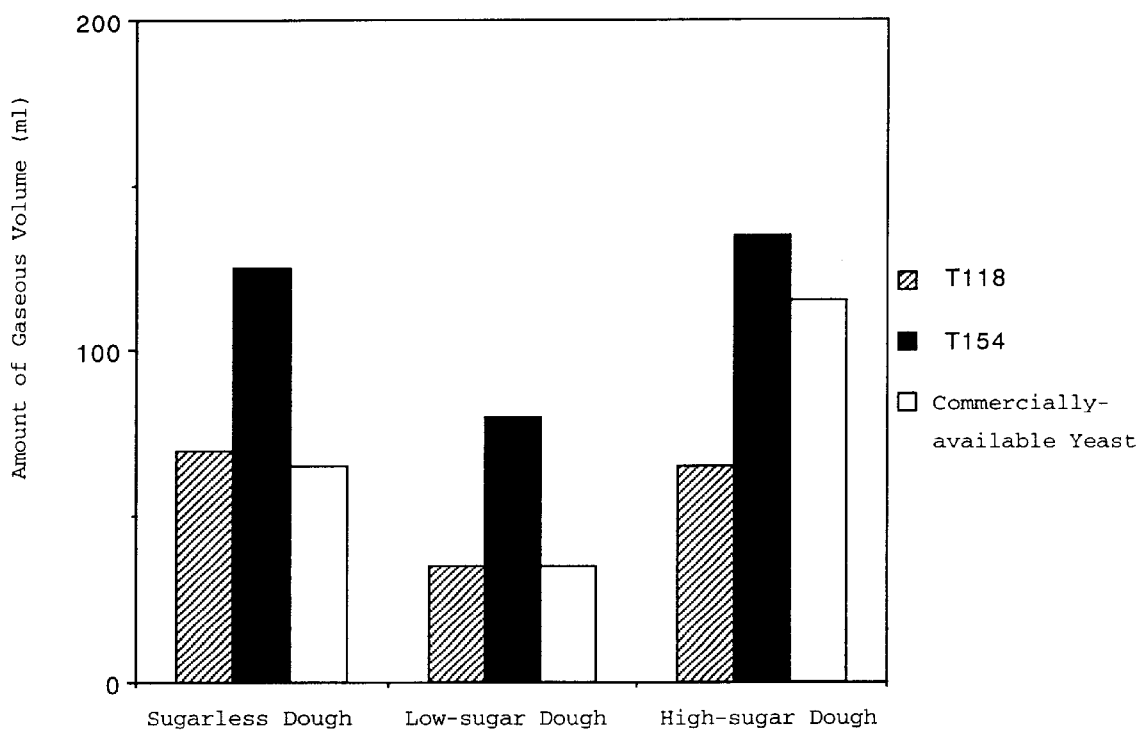
FIG. 12 shows the data of the gaseous volume of each dough sample as obtained through fermography, for which each dough sample comprising a different yeast was incubated for 60 minutes, then frozen and stored for 2 weeks, thawed, and thereafter subjected to fermography for 90 minutes.
Figure 13:
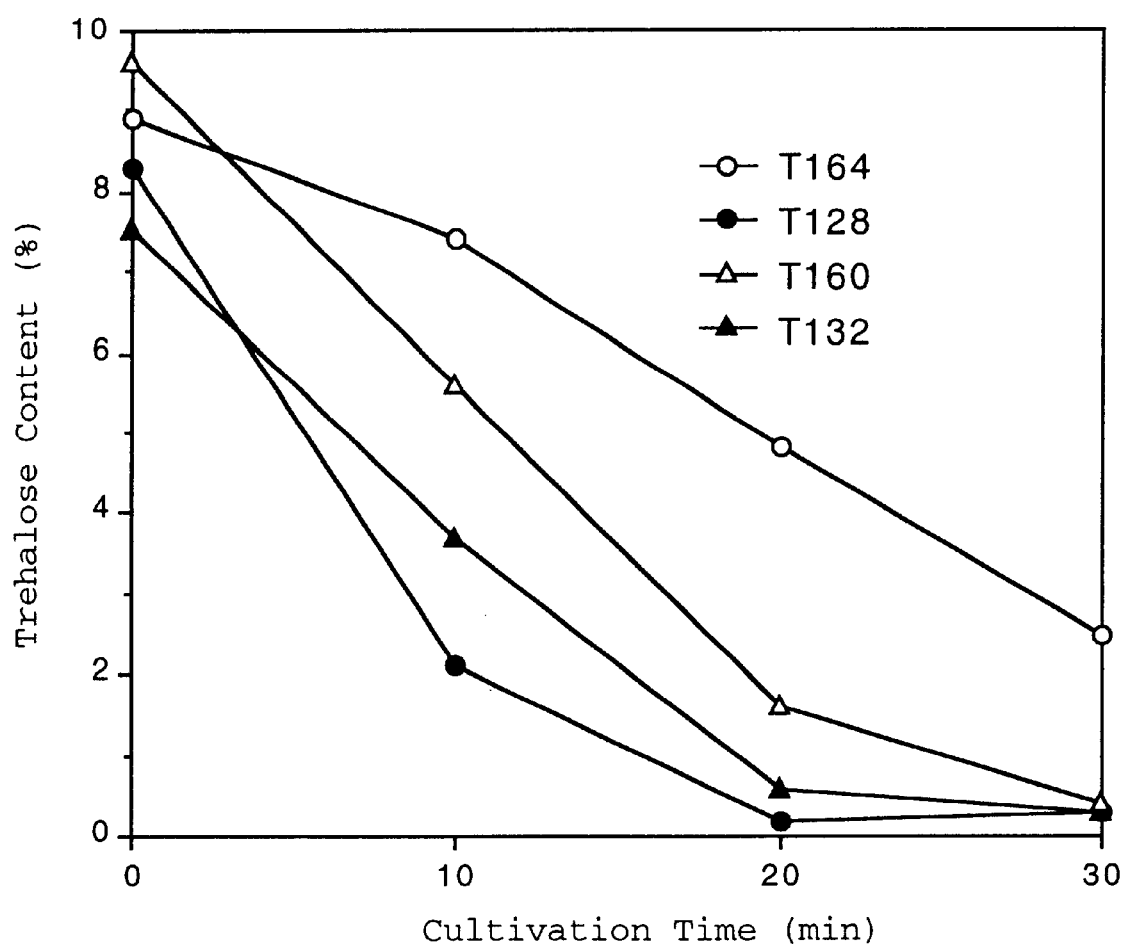
FIG. 13 shows the time-dependent variation in the trehalose content of each strain of T164, T160, T122 and T128 in culture.
Figure 14:
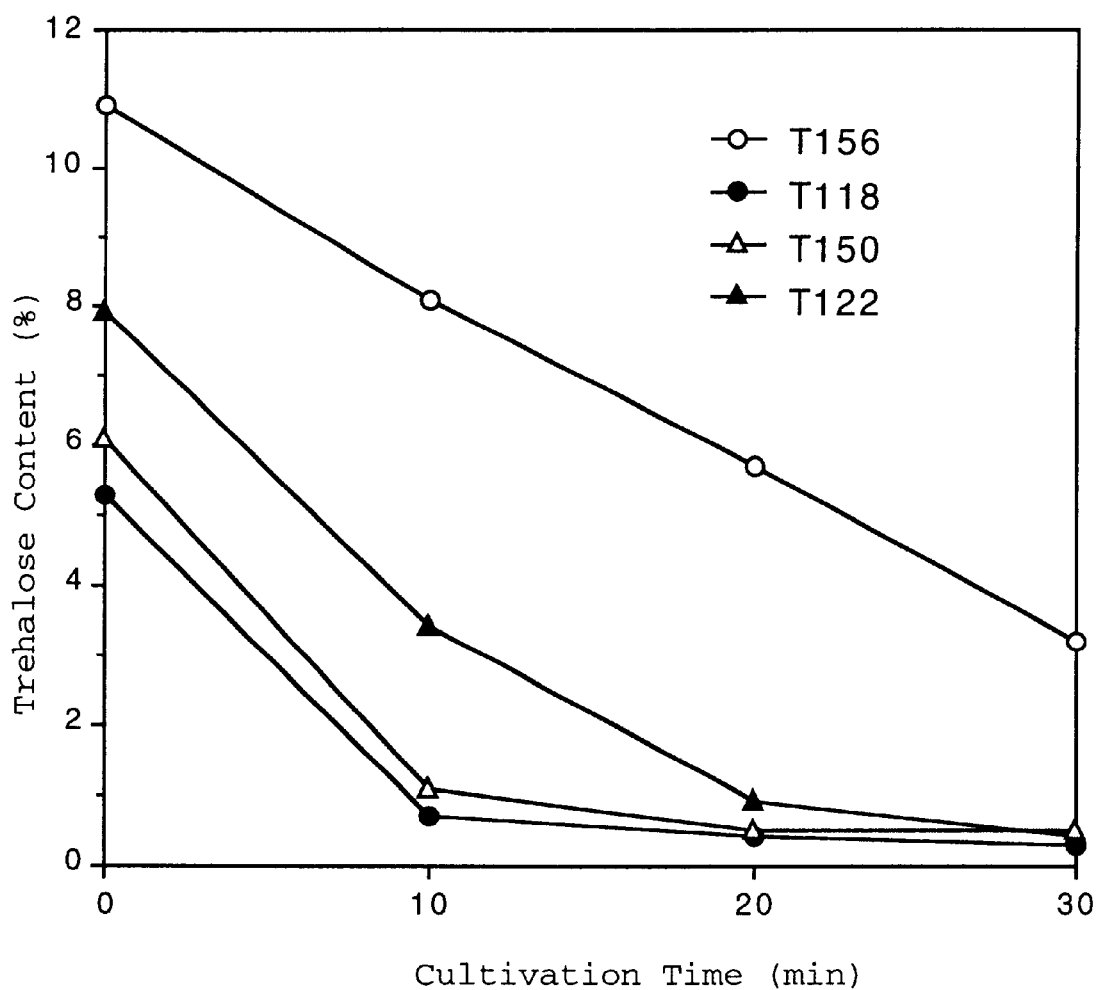
FIG. 14 shows the time-dependent variation in the trehalose content of each strain of T156, T122, T150 and T118 in culture.
Figure 15:
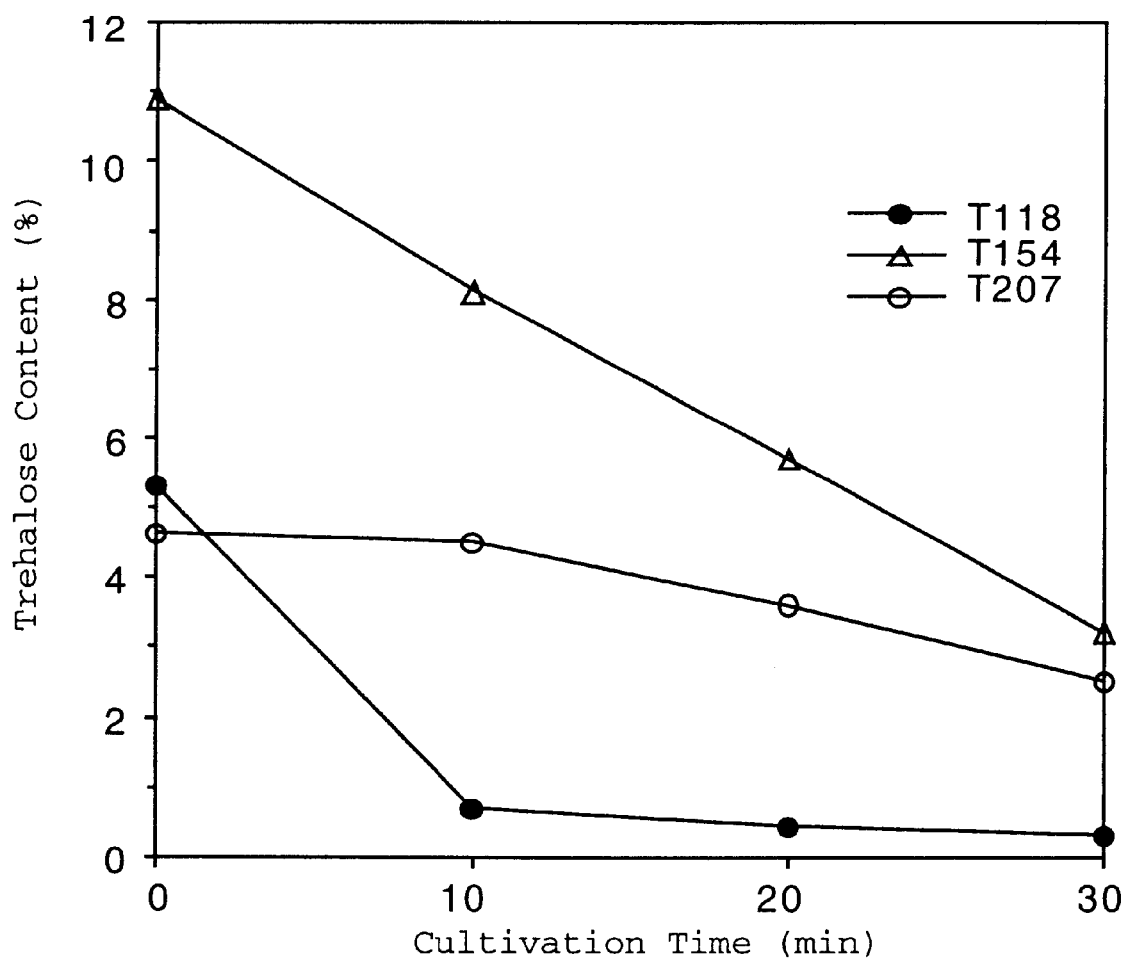
FIG. 15 shows the time-dependent variation in the trehalose content of each strain of T118, T154 and T207 in culture.
Figure 16:
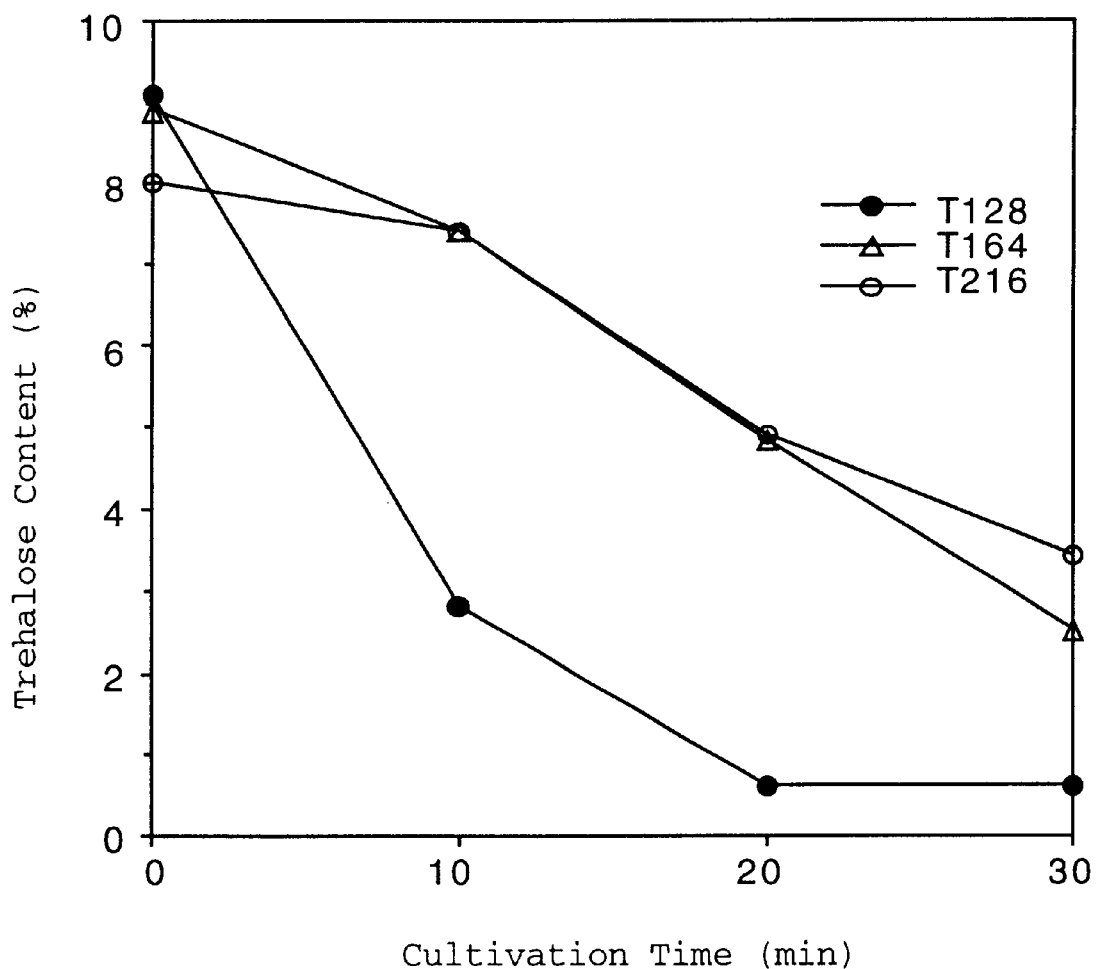
FIG. 16 shows the time-dependent variation in the trehalose content of each strain of T128, T164 and T216 in culture.
Figure 17:
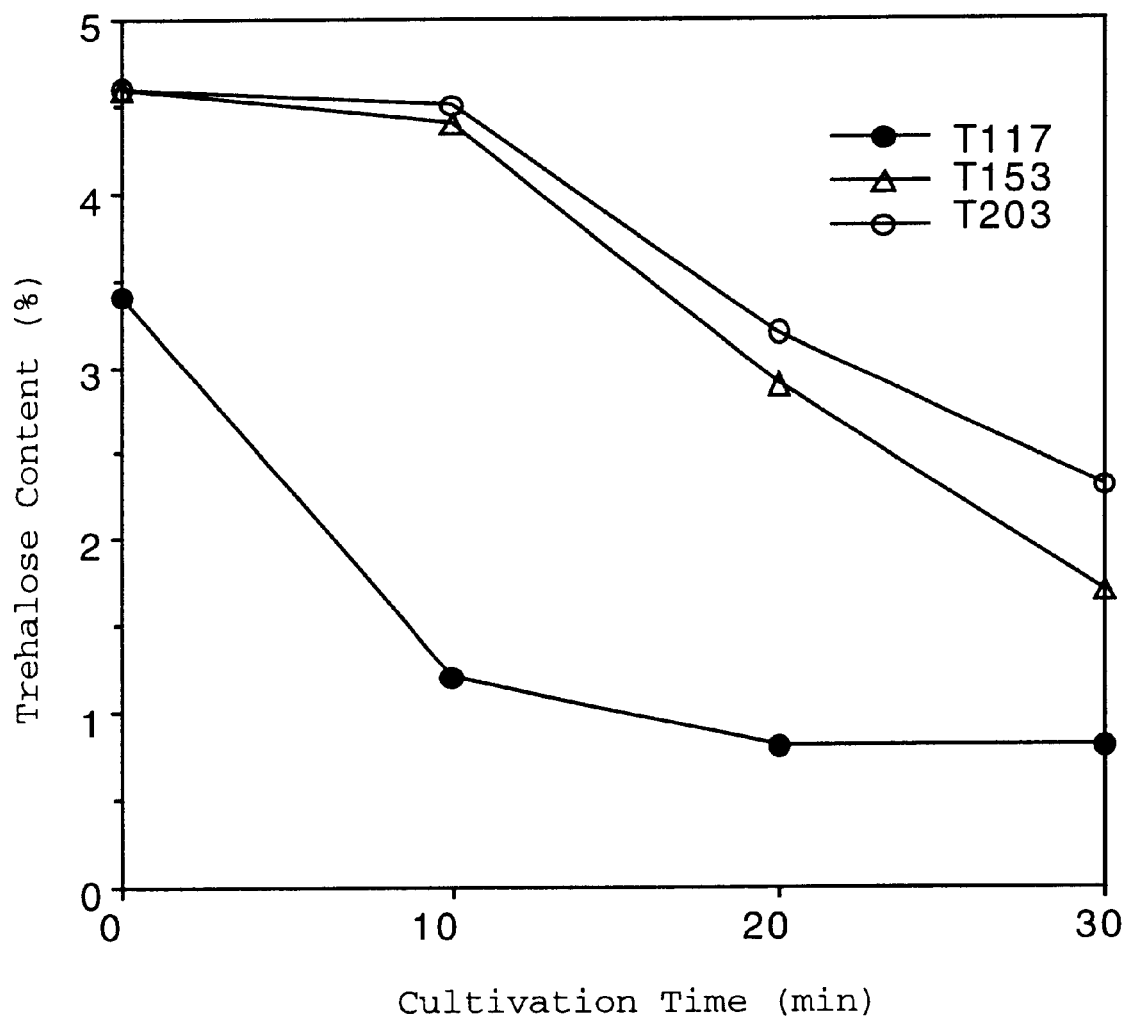
FIG. 17 shows the time-dependent variation in the trehalose content of each strain of T117, T153 and T203 in culture.

The data obtained are shown in FIG. 12.

From FIG. 12, it is known that the NTH1 gene-disrupted strain, T154 exhibited higher freezing resistance in all dough samples than the non-disrupted strain, T118. Thus, these data verify that the baker's yeast strain was made resistant to freezing through the gene disruption. In addition, as compared with that of the commercially-available yeast, the freezing resistance of the gene-disrupted strain of the invention was significantly improved. (Gas production of dough containing minijar-cultivated yeast)

Yeasts shown in Table 4, which had been cultivated in mini-jars in Example 3, were used in preparing dough samples. After having been incubated, the samples were tested to measure their gas production for 120 minutes.

As in Table 4 below, the data of gas production of non-frozen dough samples were compared with those of gas production of dough samples frozen and stored for one week.

These data verify the following: Referring to the ratio of gas production of frozen dough to that of non-frozen dough, the freezing resistance of the NTH1 gene-disrupted strain, T154 that had been cultivated in mini-jars, was higher than that of the non-disrupted strain, T118 that had also been cultivated in mini-jars, by about 14%. The NTH1 gene-disrupted strain, T207, which is different from the other gene-disrupted strains in the disrupted site of the NTH1 gene, also exhibited improved freezing resistance. Thus, these data verify that the NTH1 gene-disrupted strains produce the same result, irrespective of the disrupted site (into which was inserted URA3) of the NTH1 gene therein, so far as the NTH1 gene in those strains is inactivated.

TABLE 4

| Strain No. | Floor (initial stage) | Before Frozen | After Frozen | (after frozen)/ (before frozen) |
|---|---|---|---|---|
| T118 | 114 | 141 | 66 | 47 |
| T122 | 108 | 146 | 85 | 58 |
| T150 | 114 | 145 | 78 | 54 |
| T154 | 97 | 132 | 81 | 61 |
| T207 | 108 | 143 | 80 | 56 |
| Commercially-available ordinary yeast | 110 | 126 | 33 | 26 |
| Commercially-available yeast for frozen dough | 125 | 129 | 90 | 70 |

Amount of Gas production for 120 min (ml, in fermography)

Different strains were tested in the same manner as above. In this test, the frozen dough samples were stored for 1 week and 2 weeks.

The data obtained are shown in Table 5 below. Those data verify the following: The NTH1 gene-disrupted strain, T153 gave a higher ratio of (before frozen)/(after frozen) than the non-disrupted strain, T117, both in the dough samples frozen and stored for one week and in the dough samples frozen and stored for 2 weeks. Thus, the freezing resistance of the gene-disrupted strain T153 is higher than that of the non-disrupted strain T117.

TABLE 5

Amount of Gaseous Expansion in 120 min (ml, in fermography)

| Strain No. | Floor (initial stage) | Before Frozen | After Frozen, stored for 1 week | (before frozen)/ (after frozen) (%), 1-week stored | After Frozen, stored for 2 weeks | (before frozen)/ (after frozen) (%), 2-weeks stored |
|---|---|---|---|---|---|---|
| T117 | 116 | 147 | 96 | 65 | 80 | 54 |
| T121 | 98 | 144 | 101 | 70 | 80 | 55 |
| T149 | 97 | 137 | 99 | 72 | 92 | 67 |
| T153 | 110 | 140 | 106 | 76 | 88 | 63 |

(Gas Production of Dough Containing Yeast Cultivated in 30-liter Jars)

Yeasts shown in Tables 6 and 7 below, which had been cultivated in 30-liter jars in Example 3, were used in preparing dough samples for loaves and sugarless dough samples for French bread. The samples were incubated for 60 minutes or 120 minutes. Before and after frozen, the amount of gas production of each sample was measured. The data obtained are shown in Table 6 and Table 7. Those data verify the following: The degree of retentiveness of the living yeast in both the sugarless dough samples and the low-sugar dough samples, which had been incubated for a floor time of 60 minutes or 120 minutes, was high, before and after freezing the samples. Thus, it was confirmed that the freezing resistance of the gene-disrupted strains in those dough samples was improved high. It was also confirmed that the hybrid strains, of which one of the parent strains was an NTH1 gene-disrupted one, also exhibited improved freezing resistance.

TABLE 6

Test Data of Low-sugar Dough Samples (for loaves)

Amount of Gaseous Expansion in 120 min (ml, in fermography)

| Strain No. | Floor Time (hr) | Before Frozen | After Frozen and Stored for 1 week | Degree of Retentiveness of Living Yeast (%) | After Frozen and Stored for 2 weeks | Degree of Retentiveness of Living Yeast (%) | After Frozen and Stored for 3 weeks | Degree of Retentiveness of Living Yeast (%) |
|---|---|---|---|---|---|---|---|---|
| T118 | 1 | 145 | 108 | 74 | 100 | 69 | 96 | 66 |
| T154 |   | 138 | 115 | 83 | 107 | 76 | 103 | 75 |
| T128 |   | 159 | 137 | 86 | 121 | 76 | 117 | 74 |
| T164 |   | 157 | 140 | 89 | 127 | 81 | 123 | 78 |
| T118 | 2 | 153 | 71 | 46 | 54 | 35 | 48 | 31 |
| T154 |   | 143 | 99 | 65 | 85 | 56 | 70 | 46 |
| T128 |   | 156 | 114 | 73 | 100 | 64 | — | — |
| T164 |   | 158 | 123 | 78 | 106 | 67 | — | — |

TABLE 7

Test Data of Sugarless Dough Samples (for French bread)

Amount of Gaseous Expansion in 120 min (ml, in fermography)

| Strain No. | Floor Time (hr) | Before Frozen | After Frozen and Stored for 1 week | Degree of Retentiveness of Living Yeast (%) | After Frozen and Stored for 2 weeks | Degree of Retentiveness of Living Yeast (%) | After Frozen and Stored for 3 weeks | Degree of Retentiveness of Living Yeast (%) |
|---|---|---|---|---|---|---|---|---|
| T118 | 1 | 174 | 115 | 66 | 81 | 47 | 61 | 35 |
| T154 |   | 132 | 108 | 82 | 100 | 76 | 84 | 64 |
| T128 |   | 154 | 133 | 86 | 122 | 79 | — | — |
| T164 |   | 155 | 142 | 92 | 125 | 81 | — | — |
| T118 | 2 | 139 | 95 | 68 | 84 | 60 | 62 | 45 |
| T154 |   | 152 | 106 | 70 | 94 | 62 | 90 | 59 |
| T128 |   | 158 | 108 | 68 | 102 | 65 | — | — |
| T164 |   | 161 | 119 | 74 | 115 | 71 | — | — |

(Time-dependent Variation in Trehalose Content of Strain in Liquid Culture)

Strains as cultivated in mini-jars each were put into a device for measuring the $CO_2$ production capacity of the strain in liquid culture, in which the time-dependent variation in the trehalose content of the strain was measured. The liquid culture (F(10)) was shaken in a liquid culture device for a predetermined period of time. 20 ml of the total amount of the culture was immediately suspended in 200 ml of cold water and then centrifuged to wash the cells, which were again washed with 100 ml of cold water. The finally obtained cells were suspended in 5 ml of cold water, and the trehalose content of those cells was measured.

Figure 18:
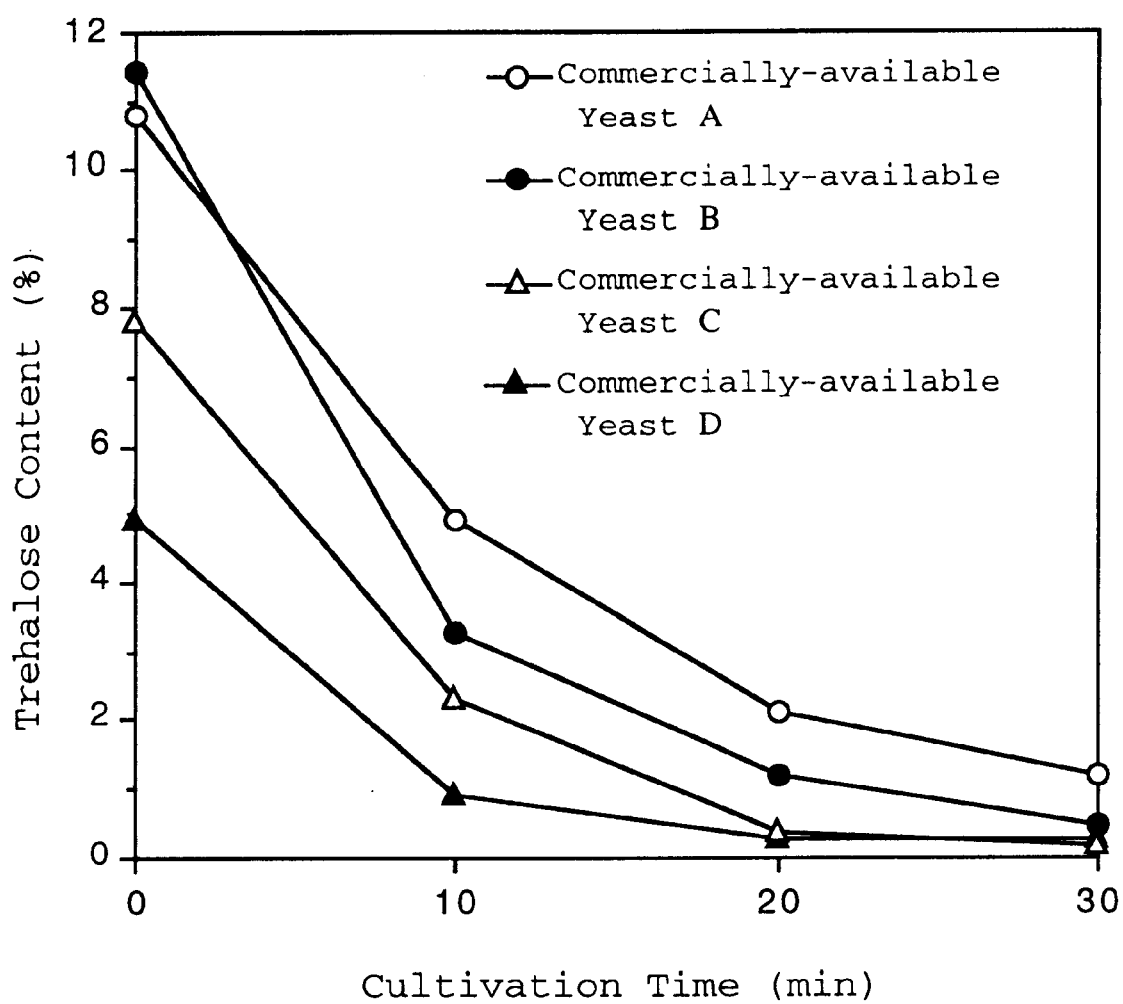
FIG. 18 shows the time-dependent variation in the trehalose content of each strain of commercially-available, freezing-resistant yeasts in culture.

The data obtained are shown in FIG. 13, FIG. 14, FIG. 15, FIG. 16, and FIG. 17. The data of commercially-available yeasts are shown in FIG. 18.

Those data verify that the reduction in the trehalose content of each NTH1 gene-disrupted strain was significantly prevented. The data indicate the time-dependent reduction in the trehalose content of the cells in liquid culture but not in dough. It is believed that the same phenomenon as in the liquid culture occurs also in the incubation of pre-frozen dough. Therefore, it is known that the trehalose content of NTH1 gene-disrupted yeast cells in dough is kept high in the step of pre-freezing the dough. The NTH1 gene-disrupted yeasts of the invention, of which the reduction in the trehalose content was significantly prevented, retained a higher trehalose content for a long period of time than the commercially-available yeasts.

EFFECTS OF THE INVENTION

According to the invention, it is possible to obtain diploid or higher polyploid, practical baker's yeasts with good frozen dough resistance by mating one or more NTH1 gene-disrupted haploid yeasts as produced through gene manipulation of disrupting the NTH1 gene of a haploid yeast, of which the diploid is practical baker's yeast.

The frozen dough-resistant,practical baker's yeast of the invention has a reduced ability of trehalose degradation at fermentation process brought by operation before freeze, whereby it possesses trehalose at high concentrate, and the dough comprising the yeast of the invention shows a long term stability of the frozen dough.

What is claimed is:

1. A biologically pure culture of *Saccharomyces cerevisiae* T154 deposited under the accession number FERM BP-5678.

2. A biologically pure culture of *Saccharomyces cerevisiae* T207 deposited under the accession number FERM BP-5679.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 2256 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 1..2253

(xi) SEQUENCE DESCRIPTION: SEQ ID NO:1:

```
ATG AGT CAA GTT AAT ACA AGC CAA GGA CCG GTA GCC CAA GGC CGT CAA        48
Met Ser Gln Val Asn Thr Ser Gln Gly Pro Val Ala Gln Gly Arg Gln
 1               5                  10                  15

AGA AGA TTA TCA TCA CTA AGT GAA TTC AAT GAT CCA TTT TCG AAC GCA        96
Arg Arg Leu Ser Ser Leu Ser Glu Phe Asn Asp Pro Phe Ser Asn Ala
            20                  25                  30

GAA GTC TAC TAT GGC CCC CCA ACA GAC CCA AGA AAG CAG AAG CAG GCA       144
Glu Val Tyr Tyr Gly Pro Pro Thr Asp Pro Arg Lys Gln Lys Gln Ala
        35                  40                  45

AAG CCC GCT AAG ATC AAC CGT ACG AGG ACT ATG AGT GTT TTC GAT AAT       192
Lys Pro Ala Lys Ile Asn Arg Thr Arg Thr Met Ser Val Phe Asp Asn
    50                  55                  60

GTA TCT CCT TTC AAG AAA ACT GGT TTT GGT AAA CTT CAA CAG ACT AGA       240
Val Ser Pro Phe Lys Lys Thr Gly Phe Gly Lys Leu Gln Gln Thr Arg
 65                  70                  75                  80

CGT GGT TCT GAG GAT GAC ACC TAT TCA AGT AGT CAA GGT AAT CGT CGT       288
Arg Gly Ser Glu Asp Asp Thr Tyr Ser Ser Ser Gln Gly Asn Arg Arg
                85                  90                  95

TTC TTT ATC GAA GAT GTC GAT AAA ACA CTT AAT GAA CTA CTG GCT GCT       336
Phe Phe Ile Glu Asp Val Asp Lys Thr Leu Asn Glu Leu Leu Ala Ala
           100                 105                 110

GAG GAT ACC GAT AAA AAT TAT CAG ATC ACC ATC GAG GAT ACC GGT CCA       384
Glu Asp Thr Asp Lys Asn Tyr Gln Ile Thr Ile Glu Asp Thr Gly Pro
       115                 120                 125

AAA GTT TTG AAA GTC GGT ACC GCA AAC TCC TAT GGC TAT AAG CAT ATT       432
Lys Val Leu Lys Val Gly Thr Ala Asn Ser Tyr Gly Tyr Lys His Ile
   130                 135                 140

AAT ATT AGG GGT ACG TAT ATG TTA TCC AAT TTG TTG CAG GAA CTA ACT       480
Asn Ile Arg Gly Thr Tyr Met Leu Ser Asn Leu Leu Gln Glu Leu Thr
145                 150                 155                 160

ATT GCG AAA AGT TTT GGT AGA CAC CAA ATT TTC TTA GAT GAA GCT CGT       528
Ile Ala Lys Ser Phe Gly Arg His Gln Ile Phe Leu Asp Glu Ala Arg
               165                 170                 175

ATA AAC GAA AAT CCC GTC AAC AGA TTA TCA AGA TTG ATA AAC ACA CAG       576
Ile Asn Glu Asn Pro Val Asn Arg Leu Ser Arg Leu Ile Asn Thr Gln
           180                 185                 190

TTC TGG AAC TCT TTG ACC AGG AGA GTT GAT CTG AAC AAC GTA GGC GAA       624
Phe Trp Asn Ser Leu Thr Arg Arg Val Asp Leu Asn Asn Val Gly Glu
       195                 200                 205

ATT GCA AAA GAT ACC AAG ATT GAT ACG CCG GGG GCA AAA AAT CCA AGA       672
Ile Ala Lys Asp Thr Lys Ile Asp Thr Pro Gly Ala Lys Asn Pro Arg
   210                 215                 220
```

```
ATC TAT GTT CCT TAT GAT TGT CCA GAA CAA TAC GAA TTT TAT GTT CAA      720
Ile Tyr Val Pro Tyr Asp Cys Pro Glu Gln Tyr Glu Phe Tyr Val Gln
225             230                 235                 240

GCT TCT CAA ATG CAT CCA TCT TTG AAA TTA GAA GTT GAA TAT TTA CCA      768
Ala Ser Gln Met His Pro Ser Leu Lys Leu Glu Val Glu Tyr Leu Pro
                245                 250                 255

AAA AAA ATA ACG GCA GAA TAC GTC AAA TCC GTC AAT GAT ACC CCC GGT      816
Lys Lys Ile Thr Ala Glu Tyr Val Lys Ser Val Asn Asp Thr Pro Gly
            260                 265                 270

TTA CTA GCA TTG GCT ATG GAA GAG CAC TTC AAT CCT TCT ACT GGT GAA      864
Leu Leu Ala Leu Ala Met Glu Glu His Phe Asn Pro Ser Thr Gly Glu
        275                 280                 285

AAA ACT CTC ATT GGT TAC CCT TAT GCT GTT CCT GGT GGT AGA TTC AAT      912
Lys Thr Leu Ile Gly Tyr Pro Tyr Ala Val Pro Gly Gly Arg Phe Asn
    290                 295                 300

GAA TTA TAT GGT TGG GAC TCC TAT ATG ATG GCA CTA GGT CTC CTA GAA      960
Glu Leu Tyr Gly Trp Asp Ser Tyr Met Met Ala Leu Gly Leu Leu Glu
305                 310                 315                 320

GCC AAC AAG ACT GAT GTT GCA AGA GGT ATG GTG GAG CAT TTT ATT TTT      1008
Ala Asn Lys Thr Asp Val Ala Arg Gly Met Val Glu His Phe Ile Phe
                325                 330                 335

GAG ATT AAT CAC TAT GGA AAA ATA TTG AAT GCT AAC AGA AGC TAC TAT      1056
Glu Ile Asn His Tyr Gly Lys Ile Leu Asn Ala Asn Arg Ser Tyr Tyr
            340                 345                 350

CTA TGT AGA TCA CAG CCC CCA TTC TTG ACT GAA ATG GCC TTG GTA GTA      1104
Leu Cys Arg Ser Gln Pro Pro Phe Leu Thr Glu Met Ala Leu Val Val
        355                 360                 365

TTC AAA AAA CTT GGT GGT AGG AGT AAT CCC GAT GCT GTG GAT TTG TTG      1152
Phe Lys Lys Leu Gly Gly Arg Ser Asn Pro Asp Ala Val Asp Leu Leu
    370                 375                 380

AAA AGA GCT TTC CAA GCA AGC ATA AAA GAG TAC AAA ACT GTT TGG ACC      1200
Lys Arg Ala Phe Gln Ala Ser Ile Lys Glu Tyr Lys Thr Val Trp Thr
385                 390                 395                 400

GCA TCT CCA AGG CTT GAT CCC GAA ACA GGC TTA TCC AGG TAC CAT CCT      1248
Ala Ser Pro Arg Leu Asp Pro Glu Thr Gly Leu Ser Arg Tyr His Pro
                405                 410                 415

AAC GGT CTC GGT ATT CCT CCG GAA ACT GAA AGT GAT CAC TTC GAT ACC      1296
Asn Gly Leu Gly Ile Pro Pro Glu Thr Glu Ser Asp His Phe Asp Thr
            420                 425                 430

GTT TTA CTA CCA TAT GCA TCG AAA CAC GGC GTT ACC TTA GAC GAA TTT      1344
Val Leu Leu Pro Tyr Ala Ser Lys His Gly Val Thr Leu Asp Glu Phe
        435                 440                 445

AAG CAA CTT TAT AAC GAT GGT AAG ATA AAG GAG CCT AAA TTG GAT GAG      1392
Lys Gln Leu Tyr Asn Asp Gly Lys Ile Lys Glu Pro Lys Leu Asp Glu
    450                 455                 460

TTT TTT CTT CAT GAC CGT GGC GTT AGA GAA TCT GGA CAC GAC ACT ACA      1440
Phe Phe Leu His Asp Arg Gly Val Arg Glu Ser Gly His Asp Thr Thr
465                 470                 475                 480

TAT AGG TTT GAG GGC GTA TGT GCC TAC CTG GCC ACT ATT GAC CTG AAT      1488
Tyr Arg Phe Glu Gly Val Cys Ala Tyr Leu Ala Thr Ile Asp Leu Asn
                485                 490                 495

TCT CTT CTT TAC AAA TAC GAG ATT GAT ATT GCG GAC TTC ATA AAG GAA      1536
Ser Leu Leu Tyr Lys Tyr Glu Ile Asp Ile Ala Asp Phe Ile Lys Glu
            500                 505                 510

TTC TGC GAC GAC AAA TAT GAA GAT CCT TTA GAC CAT TCT ATA ACA ACT      1584
Phe Cys Asp Asp Lys Tyr Glu Asp Pro Leu Asp His Ser Ile Thr Thr
        515                 520                 525

TCA GCT ATG TGG AAA GAA ATG GCC AAA ATC AGA CAA GAA AAG ATT ACC      1632
Ser Ala Met Trp Lys Glu Met Ala Lys Ile Arg Gln Glu Lys Ile Thr
```

-continued

```
          530                 535                 540
AAA TAT ATG TGG GAT GAC GAG TCG GGG TTT TTC TTT GAC TAC AAC ACA    1680
Lys Tyr Met Trp Asp Asp Glu Ser Gly Phe Phe Phe Asp Tyr Asn Thr
545                 550                 555                 560

AAA ATC AAG CAC AGA ACG TCA TAC GAA TCC GCA ACT ACA TTC TGG GCA    1728
Lys Ile Lys His Arg Thr Ser Tyr Glu Ser Ala Thr Thr Phe Trp Ala
                565                 570                 575

TTA TGG GCT GGA CTT GCC ACG AAG GAG CAA GCA CAG AAA ATG GTG GAG    1776
Leu Trp Ala Gly Leu Ala Thr Lys Glu Gln Ala Gln Lys Met Val Glu
            580                 585                 590

AAA GCA CTA CCC AAG TTA GAG ATG CTT GGA GGT TTA GCT GCA TGT ACG    1824
Lys Ala Leu Pro Lys Leu Glu Met Leu Gly Gly Leu Ala Ala Cys Thr
        595                 600                 605

GAG CGT TCT CGA GGC CCA ATT TCT ATT TCG AGA CCA ATT AGA CAA TGG    1872
Glu Arg Ser Arg Gly Pro Ile Ser Ile Ser Arg Pro Ile Arg Gln Trp
    610                 615                 620

GAC TAT CCA TTT GGT TGG GCA CCC CAT CAA ATT CTT GCT TGG GAA GGC    1920
Asp Tyr Pro Phe Gly Trp Ala Pro His Gln Ile Leu Ala Trp Glu Gly
625                 630                 635                 640

CTC CGT TCT TAT GGT TAT TTA ACT GTA ACG AAT AGG CTA GCT TAT AGA    1968
Leu Arg Ser Tyr Gly Tyr Leu Thr Val Thr Asn Arg Leu Ala Tyr Arg
                645                 650                 655

TGG CTT TTC ATG ATG ACA AAG GCT TTT GTC GAT TAT AAT GGT ATT GTG    2016
Trp Leu Phe Met Met Thr Lys Ala Phe Val Asp Tyr Asn Gly Ile Val
            660                 665                 670

GTT GAA AAA TAT GAT GTC ACA AGA GGA ACA GAT CCT CAT CGT GTT GAA    2064
Val Glu Lys Tyr Asp Val Thr Arg Gly Thr Asp Pro His Arg Val Glu
        675                 680                 685

GCA GAA TAC GGT AAT CAA GGT GCT GAC TTT AAA GGG GCA GCT ACT GAA    2112
Ala Glu Tyr Gly Asn Gln Gly Ala Asp Phe Lys Gly Ala Ala Thr Glu
    690                 695                 700

GGT TTT GGA TGG GTC AAT GCC CGT TAC ATT CTT GGT TTG AAG TAT ATG    2160
Gly Phe Gly Trp Val Asn Ala Arg Tyr Ile Leu Gly Leu Lys Tyr Met
705                 710                 715                 720

AAC AGT TAC GAA AGA AGA GAG ATT GGT GCT TGC ATT CCA CCA ATA TCA    2208
Asn Ser Tyr Glu Arg Arg Glu Ile Gly Ala Cys Ile Pro Pro Ile Ser
                725                 730                 735

TTC TTT AGC AGT TTA AGG CCT CAA GAA AGA AAC CTC TAT GGA CTA        2253
Phe Phe Ser Ser Leu Arg Pro Gln Glu Arg Asn Leu Tyr Gly Leu
            740                 745                 750

TAG                                                                 2256
```

(2) INFORMATION FOR SEQ ID NO:2:

(i) SEQUENCE CHARACTERISTICS:
        (A) LENGTH: 751 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Gln Val Asn Thr Ser Gln Gly Pro Val Ala Gln Gly Arg Gln
1               5                   10                  15

Arg Arg Leu Ser Ser Leu Ser Glu Phe Asn Asp Pro Phe Ser Asn Ala
            20                  25                  30

Glu Val Tyr Tyr Gly Pro Pro Thr Asp Pro Arg Lys Gln Lys Gln Ala
        35                  40                  45

Lys Pro Ala Lys Ile Asn Arg Thr Arg Thr Met Ser Val Phe Asp Asn
    50                  55                  60
```

```
Val Ser Pro Phe Lys Lys Thr Gly Phe Gly Lys Leu Gln Gln Thr Arg
 65                  70                  75                  80

Arg Gly Ser Glu Asp Asp Thr Tyr Ser Ser Gln Gly Asn Arg Arg
             85                  90                  95

Phe Phe Ile Glu Asp Val Asp Lys Thr Leu Asn Glu Leu Leu Ala Ala
                100                 105                 110

Glu Asp Thr Asp Lys Asn Tyr Gln Ile Thr Ile Glu Asp Thr Gly Pro
            115                 120                 125

Lys Val Leu Lys Val Gly Thr Ala Asn Ser Tyr Gly Tyr Lys His Ile
    130                 135                 140

Asn Ile Arg Gly Thr Tyr Met Leu Ser Asn Leu Leu Gln Glu Leu Thr
145                 150                 155                 160

Ile Ala Lys Ser Phe Gly Arg His Gln Ile Phe Leu Asp Glu Ala Arg
                165                 170                 175

Ile Asn Glu Asn Pro Val Asn Arg Leu Ser Arg Leu Ile Asn Thr Gln
            180                 185                 190

Phe Trp Asn Ser Leu Thr Arg Arg Val Asp Leu Asn Asn Val Gly Glu
        195                 200                 205

Ile Ala Lys Asp Thr Lys Ile Asp Thr Pro Gly Ala Lys Asn Pro Arg
    210                 215                 220

Ile Tyr Val Pro Tyr Asp Cys Pro Glu Gln Tyr Glu Phe Tyr Val Gln
225                 230                 235                 240

Ala Ser Gln Met His Pro Ser Leu Lys Leu Glu Val Glu Tyr Leu Pro
                245                 250                 255

Lys Lys Ile Thr Ala Glu Tyr Val Lys Ser Val Asn Asp Thr Pro Gly
            260                 265                 270

Leu Leu Ala Leu Ala Met Glu Glu His Phe Asn Pro Ser Thr Gly Glu
        275                 280                 285

Lys Thr Leu Ile Gly Tyr Pro Tyr Ala Val Pro Gly Gly Arg Phe Asn
    290                 295                 300

Glu Leu Tyr Gly Trp Asp Ser Tyr Met Met Ala Leu Gly Leu Leu Glu
305                 310                 315                 320

Ala Asn Lys Thr Asp Val Ala Arg Gly Met Val Glu His Phe Ile Phe
                325                 330                 335

Glu Ile Asn His Tyr Gly Lys Ile Leu Asn Ala Asn Arg Ser Tyr Tyr
            340                 345                 350

Leu Cys Arg Ser Gln Pro Pro Phe Leu Thr Glu Met Ala Leu Val Val
        355                 360                 365

Phe Lys Lys Leu Gly Gly Arg Ser Asn Pro Asp Ala Val Asp Leu Leu
    370                 375                 380

Lys Arg Ala Phe Gln Ala Ser Ile Lys Glu Tyr Lys Thr Val Trp Thr
385                 390                 395                 400

Ala Ser Pro Arg Leu Asp Pro Glu Thr Gly Leu Ser Arg Tyr His Pro
                405                 410                 415

Asn Gly Leu Gly Ile Pro Pro Glu Thr Glu Ser Asp His Phe Asp Thr
            420                 425                 430

Val Leu Leu Pro Tyr Ala Ser Lys His Gly Val Thr Leu Asp Glu Phe
        435                 440                 445

Lys Gln Leu Tyr Asn Asp Gly Lys Ile Lys Glu Pro Lys Leu Asp Glu
    450                 455                 460

Phe Phe Leu His Asp Arg Gly Val Arg Glu Ser Gly His Asp Thr Thr
465                 470                 475                 480
```

```
Tyr Arg Phe Glu Gly Val Cys Ala Tyr Leu Ala Thr Ile Asp Leu Asn
            485                 490                 495

Ser Leu Leu Tyr Lys Tyr Glu Ile Asp Ile Ala Asp Phe Ile Lys Glu
            500                 505                 510

Phe Cys Asp Asp Lys Tyr Glu Asp Pro Leu Asp His Ser Ile Thr Thr
            515                 520                 525

Ser Ala Met Trp Lys Glu Met Ala Lys Ile Arg Gln Glu Lys Ile Thr
        530                 535                 540

Lys Tyr Met Trp Asp Asp Glu Ser Gly Phe Phe Asp Tyr Asn Thr
545                 550                 555                 560

Lys Ile Lys His Arg Thr Ser Tyr Glu Ser Ala Thr Thr Phe Trp Ala
                565                 570                 575

Leu Trp Ala Gly Leu Ala Thr Lys Glu Gln Ala Gln Lys Met Val Glu
            580                 585                 590

Lys Ala Leu Pro Lys Leu Glu Met Leu Gly Gly Leu Ala Ala Cys Thr
            595                 600                 605

Glu Arg Ser Arg Gly Pro Ile Ser Ile Ser Arg Pro Ile Arg Gln Trp
    610                 615                 620

Asp Tyr Pro Phe Gly Trp Ala Pro His Gln Ile Leu Ala Trp Glu Gly
625                 630                 635                 640

Leu Arg Ser Tyr Gly Tyr Leu Thr Val Thr Asn Arg Leu Ala Tyr Arg
            645                 650                 655

Trp Leu Phe Met Met Thr Lys Ala Phe Val Asp Tyr Asn Gly Ile Val
                660                 665                 670

Val Glu Lys Tyr Asp Val Thr Arg Gly Thr Asp Pro His Arg Val Glu
            675                 680                 685

Ala Glu Tyr Gly Asn Gln Gly Ala Asp Phe Lys Gly Ala Ala Thr Glu
        690                 695                 700

Gly Phe Gly Trp Val Asn Ala Arg Tyr Ile Leu Gly Leu Lys Tyr Met
705                 710                 715                 720

Asn Ser Tyr Glu Arg Arg Glu Ile Gly Ala Cys Ile Pro Pro Ile Ser
            725                 730                 735

Phe Phe Ser Ser Leu Arg Pro Gln Glu Arg Asn Leu Tyr Gly Leu
            740                 745                 750

(2) INFORMATION FOR SEQ ID NO:3:

(i) SEQUENCE CHARACTERISTICS:
        (A) LENGTH: 804 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..801

(xi) SEQUENCE DESCRIPTION: SEQ ID NO:3:

ATG TCG AAA GCT ACA TAT AAG GAA CGT GCT GCT ACT CAT CCT AGT CCT     48
Met Ser Lys Ala Thr Tyr Lys Glu Arg Ala Ala Thr His Pro Ser Pro
              5                  10                  15

GTT GCT GCC AAG CTA TTT AAT ATC ATG CAC GAA AAG CAA ACA AAC TTG     96
Val Ala Ala Lys Leu Phe Asn Ile Met His Glu Lys Gln Thr Asn Leu
         20                  25                  30

TGT GCT TCA TTG GAT GTT CGT ACC ACC AAG GAA TTA CTG GAG TTA GTT    144
Cys Ala Ser Leu Asp Val Arg Thr Thr Lys Glu Leu Leu Glu Leu Val
     35                  40                  45
```

```
GAA GCA TTA GGT CCC AAA ATT TGT TTA CTA AAA ACA CAT GTG GAT ATC    192
Glu Ala Leu Gly Pro Lys Ile Cys Leu Leu Lys Thr His Val Asp Ile
         50              55                  60

TTG ACT GAT TTT TCC ATG GAG GGC ACA GTT AAG CCG CTA AAG GCA TTA    240
Leu Thr Asp Phe Ser Met Glu Gly Thr Val Lys Pro Leu Lys Ala Leu
65              70                  75                  80

TCC GCC AAG TAC AAT TTT TTA CTC TTC GAA GAC AGA AAA TTT GCT GAC    288
Ser Ala Lys Tyr Asn Phe Leu Leu Phe Glu Asp Arg Lys Phe Ala Asp
                    85                  90                  95

ATT GGT AAT ACA GTC AAA TTG CAG TAC TCT GCG GGT GTA TAC AGA ATA    336
Ile Gly Asn Thr Val Lys Leu Gln Tyr Ser Ala Gly Val Tyr Arg Ile
                100                 105                 110

GCA GAA TGG GCA GAC ATT ACG AAT GCA CAC GGT GTG GTG GGC CCA GGT    384
Ala Glu Trp Ala Asp Ile Thr Asn Ala His Gly Val Val Gly Pro Gly
            115                 120                 125

ATT GTT AGC GGT TTG AAG CAG GCG GCA GAA GAA GTA ACA AAG GAA CCT    432
Ile Val Ser Gly Leu Lys Gln Ala Ala Glu Glu Val Thr Lys Glu Pro
        130                 135                 140

AGA GGC CTT TTG ATG TTA GCA GAA TTG TCA TGC AAG GGC TCC CTA TCT    480
Arg Gly Leu Leu Met Leu Ala Glu Leu Ser Cys Lys Gly Ser Leu Ser
145                 150                 155                 160

ACT GGA GAA TAT ACT AAG GGT ACT GTT GAC ATT GCG AAG AGC GAC AAA    528
Thr Gly Glu Tyr Thr Lys Gly Thr Val Asp Ile Ala Lys Ser Asp Lys
                165                 170                 175

GAT TTT GTT ATC GGC TTT ATT GCT CAA AGA GAC ATG GGT GGA AGA GAT    576
Asp Phe Val Ile Gly Phe Ile Ala Gln Arg Asp Met Gly Gly Arg Asp
            180                 185                 190

GAA GGT TAC GAT TGG TTG ATT ATG ACA CCC GGT GTG GGT TTA GAT GAC    624
Glu Gly Tyr Asp Trp Leu Ile Met Thr Pro Gly Val Gly Leu Asp Asp
        195                 200                 205

AAG GGA GAC GCA TTG GGT CAA CAG TAT AGA ACC GTG GAT GAT GTG GTC    672
Lys Gly Asp Ala Leu Gly Gln Gln Tyr Arg Thr Val Asp Asp Val Val
    210                 215                 220

TCT ACA GGA TCT GAC ATT ATT ATT GTT GGA AGA GGA CTA TTT GCA AAG    720
Ser Thr Gly Ser Asp Ile Ile Ile Val Gly Arg Gly Leu Phe Ala Lys
225                 230                 235                 240

GGA AGG GAT GCT AAG GTA GAG GGT GAA CGT TAC AGA AAA GCA GGC TGG    768
Gly Arg Asp Ala Lys Val Glu Gly Glu Arg Tyr Arg Lys Ala Gly Trp
                245                 250                 255

GAA GCA TAT TTG AGA AGA TGC GGC CAG CAA AAC TAA                    804
Glu Ala Tyr Leu Arg Arg Cys Gly Gln Gln Asn
            260                 265
```

(2) INFORMATION FOR SEQ ID NO:4:

(i) SEQUENCE CHARACTERISTICS:
        (A) LENGTH: 267 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Lys Ala Thr Tyr Lys Glu Arg Ala Ala Thr His Pro Ser Pro
1               5                   10                  15

Val Ala Ala Lys Leu Phe Asn Ile Met His Glu Lys Gln Thr Asn Leu
            20                  25                  30

Cys Ala Ser Leu Asp Val Arg Thr Thr Lys Glu Leu Leu Glu Leu Val
        35                  40                  45

Glu Ala Leu Gly Pro Lys Ile Cys Leu Leu Lys Thr His Val Asp Ile
```

```
                    50                      55                      60
Leu Thr Asp Phe Ser Met Glu Gly Thr Val Lys Pro Leu Lys Ala Leu
 65                      70                      75                      80

Ser Ala Lys Tyr Asn Phe Leu Leu Phe Glu Asp Arg Lys Phe Ala Asp
                 85                      90                      95

Ile Gly Asn Thr Val Lys Leu Gln Tyr Ser Ala Gly Val Tyr Arg Ile
                100                     105                     110

Ala Glu Trp Ala Asp Ile Thr Asn Ala His Gly Val Val Gly Pro Gly
            115                     120                     125

Ile Val Ser Gly Leu Lys Gln Ala Ala Glu Glu Val Thr Lys Glu Pro
        130                     135                     140

Arg Gly Leu Leu Met Leu Ala Glu Leu Ser Cys Lys Gly Ser Leu Ser
145                     150                     155                     160

Thr Gly Glu Tyr Thr Lys Gly Thr Val Asp Ile Ala Lys Ser Asp Lys
                165                     170                     175

Asp Phe Val Ile Gly Phe Ile Ala Gln Arg Asp Met Gly Gly Arg Asp
                180                     185                     190

Glu Gly Tyr Asp Trp Leu Ile Met Thr Pro Gly Val Gly Leu Asp Asp
            195                     200                     205

Lys Gly Asp Ala Leu Gly Gln Gln Tyr Arg Thr Val Asp Asp Val Val
        210                     215                     220

Ser Thr Gly Ser Asp Ile Ile Ile Val Gly Arg Gly Leu Phe Ala Lys
225                     230                     235                     240

Gly Arg Asp Ala Lys Val Glu Gly Glu Arg Tyr Arg Lys Ala Gly Trp
                245                     250                     255

Glu Ala Tyr Leu Arg Arg Cys Gly Gln Gln Asn
                260                     265
```